United States Patent [19]

Weaver et al.

[11] Patent Number: 5,274,072
[45] Date of Patent: Dec. 28, 1993

[54] POLYESTER COMPOSITION HAVING COPOLYMERIZED THEREIN A LIGHT ABSORBING COMPOUND

[75] Inventors: Max A. Weaver; James J. Krutak; Clarence A. Coates, Jr.; William W. Parham; Wayne P. Pruett, all of Kingsport; Samuel D. Hilbert, Jonesborough, all of Tenn.

[73] Assignee: Eastman Kodak Company, Rochester, N.Y.

[21] Appl. No.: 878,273

[22] Filed: May 4, 1992

[51] Int. Cl.⁵ .................. C08G 63/08; C07D 277/62; C07D 307/02
[52] U.S. Cl. .................... 528/354; 548/180; 548/204; 548/468; 548/517; 549/32; 549/60; 549/70; 549/320; 549/474; 549/479
[58] Field of Search ............. 528/354; 548/180, 204, 548/468, 517; 549/32, 60, 70, 320, 474, 479

[56] References Cited

U.S. PATENT DOCUMENTS

| 3,661,899 | 5/1972 | Ford et al. | 524/111 |
| 4,617,373 | 10/1986 | Pruett et al. | 528/288 |
| 5,032,670 | 7/1991 | Parham et al. | 528/220 |
| 5,106,942 | 4/1992 | Krutak et al. | 528/272 |

OTHER PUBLICATIONS

"Journal of Organic Chemistry", Ford et al, vol. 32, pp. 173-177.

Primary Examiner—John Kight, III
Assistant Examiner—T. Mosley
Attorney, Agent, or Firm—Bernard J. Graves, Jr.; William P. Heath, Jr.

[57] ABSTRACT

Provided are certain novel substituted 2(5H)furanone compounds which are useful as ultraviolet/visible light absorbing compounds. Also provided are polyester compositions having such compounds copolymerized therein and shaped or formed articles comprised of such polyester compositions.

33 Claims, No Drawings

POLYESTER COMPOSITION HAVING COPOLYMERIZED THEREIN A LIGHT ABSORBING COMPOUND

FIELD OF THE INVENTION

This invention belongs to the field of organic chemistry. In particular, this invention provides certain novel 2(5H) furanone compounds and polyester compositions having such compounds copolymerized therein.

BACKGROUND OF THE INVENTION

It is known that one may prepare methine compounds from 2(5H)furanones containing cyano, p-nitrophenyl, p-cyanophenyl, optionally substituted carbamoyl and carboxylic acid ester groups (see, for example, U.S. Pat. No. 3,661,899 and U.S. Pat. No. 4,617,373). The methine compounds disclosed in these two patents have a high degree of volatility and have a tendency to sublime, exude and migrate from polymeric substrates colored with them. Also, when applied to polyester fabric as textile dyes from a finely divided state they have a tendency to be removed from the fabric via washing and are sensitive to changes in pH. U.S. Pat. No. 4,617,373 shows that the compounds can be copolymerized into polyester compositions to reduce the sublimation, migration, etc. by incorporating reactive groups, e.g. ester groups, into the colorants and adding the colorants prior to the polyester forming reaction. Compounds such as those of Examples 20, 125, 126, 147, 195, etc. have a reactive group present only on the aldehyde portion of the reactant and not on the 2(5H) furanone active methylene portion of the methine compound; in this fashion, these compounds are incorporated into the polyester polymer, but they do not provide the greatest degree of nonextractability and lowest level of toxicity hazard. This is believed to occur because the methine linkage may be destroyed, e.g. by exposure to light, leaving the 2(5H) furanone moiety unattached to the polymer and thus rendering it extractable (see Example 761). In contrast, when the furanone moiety contains a reactive ester group in the 3-position (see Example 22 of U.S. Pat. No. 4,617,373) this moiety may still be attached to the polymer even though the methine linkage might be destroyed. The presence of the ester groups, however, as compared to a 3-cyano group, results in a detrimental hypsochromic shift in the absorption maximum (shift to shorter wavelengths) and a lowering of the color value (extinction coefficient) (see Table 1). In contrast, the presence of the reactive ester group on the 3-heteroaryl 2 (5H) furanone compounds of the present invention does not cause such a significant hypsochromic shift and lowering of the extinction coefficient (see Table 1 below).

SUMMARY OF THE INVENTION

The present invention provides certain novel substituted 2(5H)furanone.compounds which contain a heteroaryl group in the 3-position; new UV/visible light absorbing compounds derived therefrom; and thermoplastic polymers containing these new compounds. The light absorbing compounds are thermally stable and have low volatility, thus rendering them useful for imparting light absorbing properties to a variety of thermoplastic polymers. Their excellent thermal stability allows them to be added during high temperature polymerizations such as that encountered in preparation of polyesters or to be melt blended with the polymeric substrate. Further, when reactive groups are present, the light absorbing compounds can be copolymerized to produce polymers from which the light absorbing components do not extract, sublime, exude, migrate, etc.

DETAILED DESCRIPTION OF THE INVENTION

The present invention provides light absorbing compounds of formulae (II) and (III):

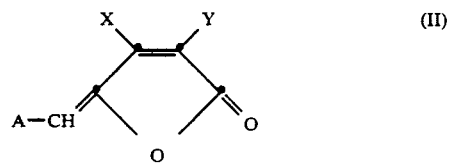

and

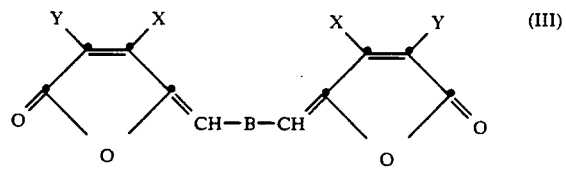

wherein X is an unsubstituted or substituted phenyl radical, wherein Y is an unsubstituted or substituted benzoxazol-2-yl or benzothiazol-2-yl radical, wherein A is selected from groups of the formulae

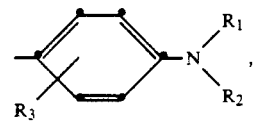

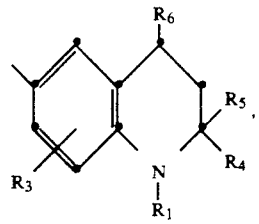

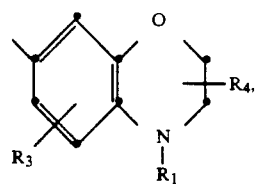

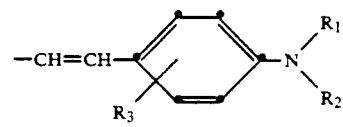

-continued
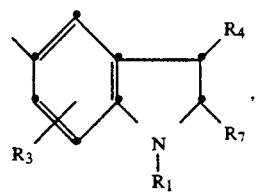
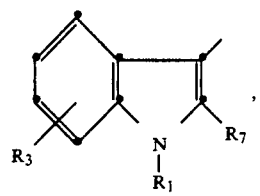
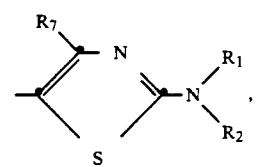
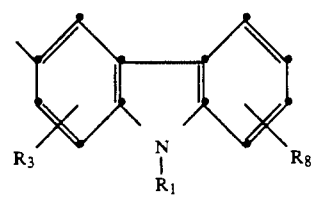
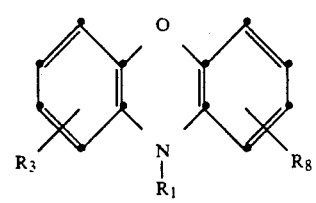
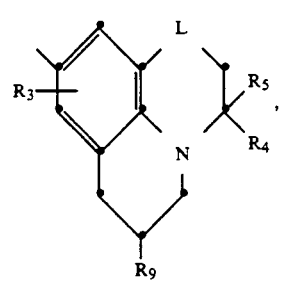
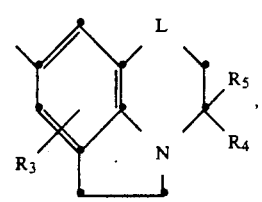
-continued
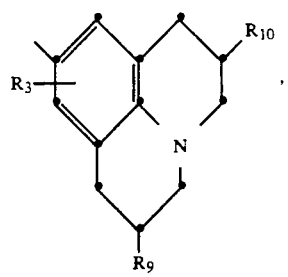
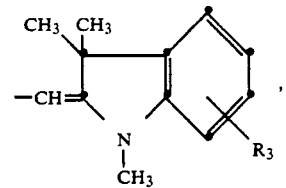
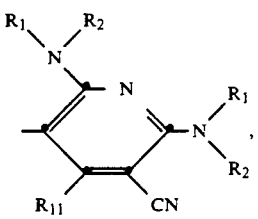
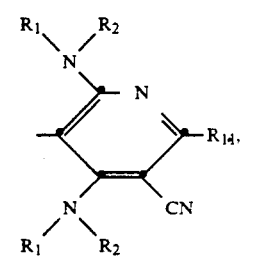
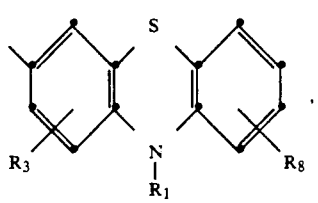
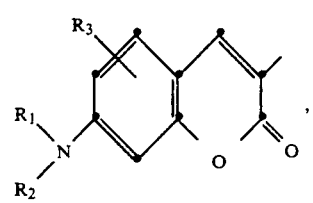
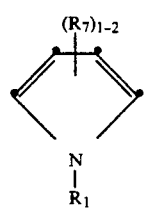

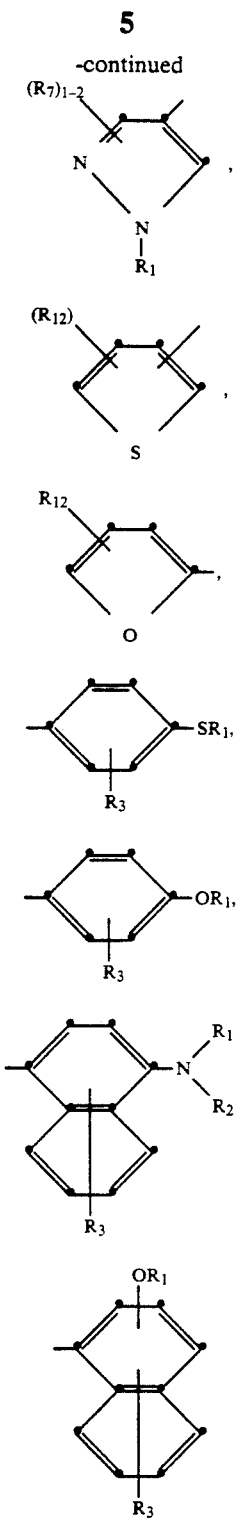

and B is selected from the following formulae:

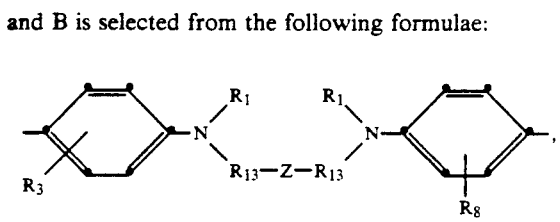

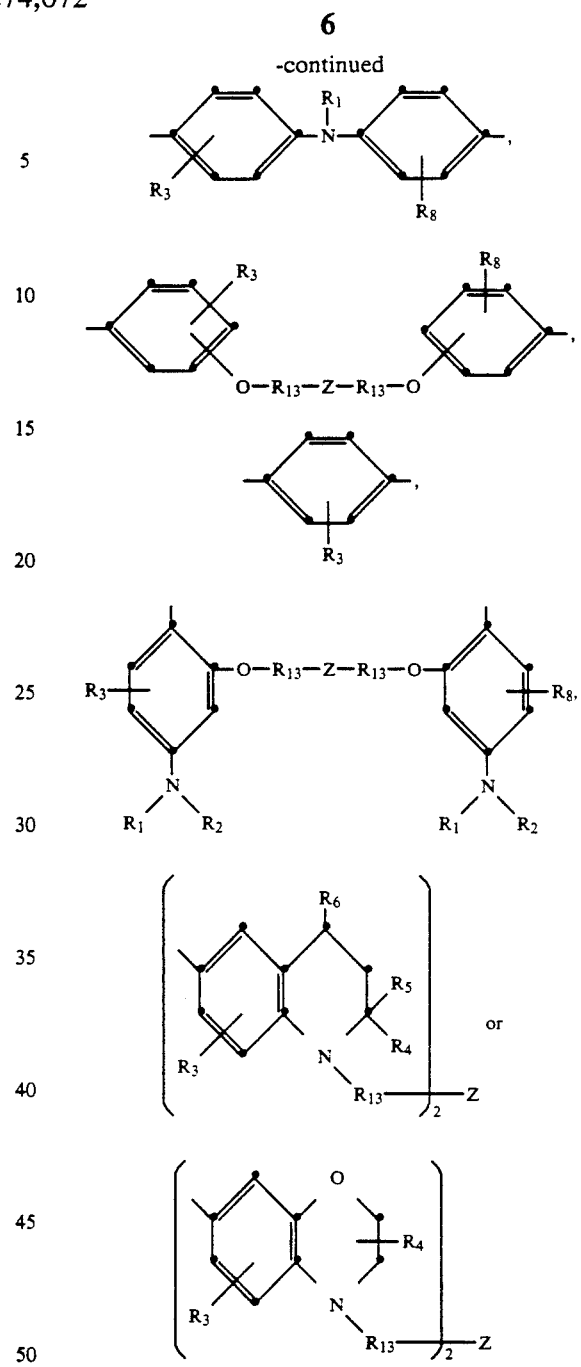

wherein $R_1$ and $R_2$ are selected from unsubstituted alkyl, alkenyl, alkynyl, cycloalkyl or phenyl and substituted alkyl, cycloalkyl and phenyl; or $R_1$ and $R_2$ are combined with the nitrogen to which they are attached to form an A radical having the formula

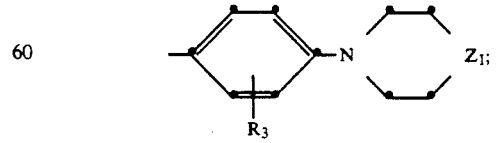

wherein $Z_1$ is selected from a convalent bond, —$CH_2$—, —O—, —S—, —$SO_2$—, —CO—, —$CO_2$—, —NH—, —N($R_1$)—, N(COR$_1$)— or —N($SO_2R_1$)—; $R_3$ and $R_8$ are hydrogen or 1–2 substituents selected from lower alkyl, lower alkoxy or halogen; $R_4$, $R_5$ and $R_6$ are hydrogen or lower alkyl; $R_7$ is hydrogen, lower alkyl, phenyl or substituted phenyl; $R_9$ and $R_{10}$ are selected from hydrogen, lower alkyl, lower alkoxy, hydroxy, halogen or alkanoyloxy; $R_{11}$ is lower alkyl, phenyl or substituted phenyl; $R_{12}$ is hydrogen or 1-2 substituents selected from lower alkyl; lower alkoxy; lower alkylthio; alkenyl; cycloalkyl; lower alkyl substituted with lower alkoxy, hydroxy, alkanoyloxy or phenyl; phenyl; substituted phenyl or halogen; $R_{13}$ is lower alkylene, substituted lower alkylene, alkylene oxyalkylene, phenylene, substituted phenylene, phenylenealkylene, substituted phenylenealkylene or cycloalkylene; Z is a direct bond, —OCO₂—, —O₂C—, —O—, —SO₂—, —S—, —S—S—, $R_1SO_2$—N=, —O₂C— lower alkylene —CO₂—, phenylene, —O₂C—C-phenylene-CO₂—, —O₂C— substituted phenylene—CO₂—, —O₂CN-H—alkylene—NHCO₂—, —O₂CNH— phenylene—NHCO₂— or —O₂CNH—substituted phenylene—NHCO₂; and L is selected from a direct bond, —O—, —CH₂— or —CH(CH₃)—.

As a preferred embodiment of this aspect of the invention, there is provided the compounds of the above formulae wherein A is selected from groups of the formula

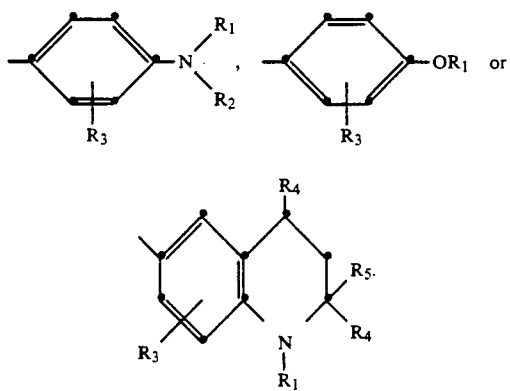

The terms "alkyl" and "lower alkyl" are used to represent straight or branched chain $C_1$-$C_{12}$ alkyl group and a $C_1$-$C_6$ alkyl group, respectively.

The term "substituted alkyl" is used to represent an alkyl group substituted with one or more of the following groups: cycloalkyl and substituted cycloalkyl; phenyl and substituted phenyl; cyano; halogen; 2-pyrrolidino; phthalimidino; vinylsulfonyl; acrylamido; o-benzoic sulfimido; alkoxy; alkoxyalkoxy; cyanoalkoxy; hydroxy; hydroxyalkoxy; phenoxy; phenoxy substituted with lower alkyl, lower alkoxy or halogen; groups of the formulae:

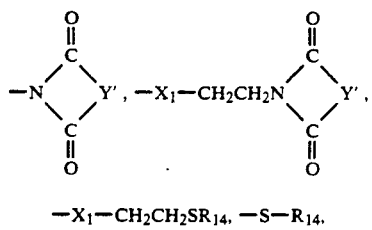

—X₁—CH₂CH₂SR₁₄, —S—R₁₄,

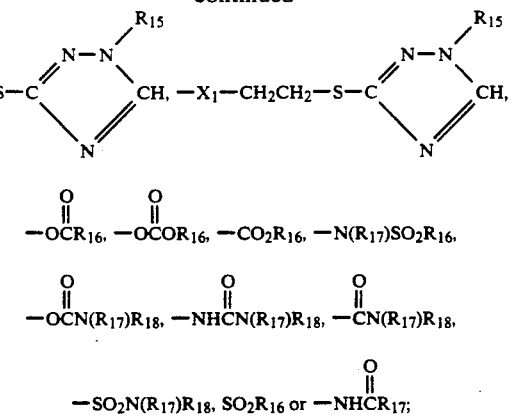

—OCR₁₆, —OCOR₁₆, —CO₂R₁₆, —N(R₁₇)SO₂R₁₆,

—OCN(R₁₇)R₁₈, —NHCN(R₁₇)R₁₈, —CN(R₁₇)R₁₈,

—SO₂N(R₁₇)R₁₈, SO₂R₁₆ or —NHCR₁₇;

wherein $X_1$ is selected from —O—, —S— or —SO₂—; $Y_1$ is selected from $C_2$-$C_3$ alkylene, vinylene, o-phenylene and o-phenylene substituted with lower alkyl, lower alkoxy, halogen, carboxy, alkoxycarbonyl or nitro; —OCH₂—; —OCH₂CH₂—; —CH₂OCH₂—; —S—CH—; —CH₂SCH₂—; —NHCH₂—; —NHCH₂CH₂—; —N(alkyl)CH₂—; N(alkyl)CH₂CH— or NHC(C₆H₅)₂—; $R_{14}$ is selected from lower alkyl; cycloalkyl; phenyl; phenyl substituted with one or more groups selected from lower alkyl, lower alkoxy or halogen; a heterocyclic ring selected from pyridyl, pyrimidinyl, benzoxazolyl, benzothiazolyl, benzimidazol, 1,3,4-thiadiazolyl, and 1,3,4-oxadiazolyl, said heterocyclic rings optionally substituted with one or more groups selected from lower alkyl, lower alkoxy or halogen; $R_{15}$ is selected from hydrogen, lower alkyl; alkyl substituted with hydroxy, alkanoyloxy, lower alkoxy, halogen, cyano, carbalkoxy or phenyl; $R_{16}$ is selected from cycloalkyl; cycloalkyl substituted with lower alkyl; allyl; phenyl; phenyl substituted with one or more groups selected from lower alkyl, lower alkoxy or halogen; lower alkyl; lower alkyl substituted with one or more groups selected from lower alkoxy, halogen, phenyl, cyano, cycloalkyl, phenoxy, lower alkylthio, hydroxy, alkanoyloxy, alkoxycarbonyl or lower alkylsulfonyl; and $R_{17}$ and $R_{18}$ are each independently selected from hydrogen or those groups represented by $R_{16}$.

The term "substituted phenyl" is used to represent a phenyl radical substituted with one or more substituents selected from the following: lower alkyl; lower alkoxy; halogen; hydroxy; cyano; NHCOR₁₇; —N(R₁₇)SO₂R₁₆; SO₂R₁₆; CO₂R₁₆; lower alkyl substituted with hydroxy, lower alkoxy, halogen or alkanoyloxy.

The term "alkanoyloxy" refers to a carbonyloxy group. In other words, the $C_2$ alkanoyloxy group is propionyloxy.

In the above formulae, the term "cycloalkyl" preferably denotes a $C_5$-$C_7$ cycloalkyl group. Examples include cyclopentyl, cyclohexyl, and cycloheptyl.

The term "substituted cycloalkyl" refers to a $C_5$-$C_7$ cycloalkyl group substituted with one or more groups selected from the group consisting of lower alkyl, lower alkoxy, hydroxy, and alkanoyloxy.

The term "alkoxycarbonyl" preferably refers to a $C_1$-$C_6$ alkoxy group bonded to a carbonyl function. For example, the $C_2$ alkoxycarbonyl group is ethoxycarbonyl.

The term "alkanoyloxy" preferably denotes a $C_1$–$C_6$ alkylcarbonyloxy group. In other words, the $C_2$ alkanoyloxy group is propionyloxy.

The terms "alkenyl" and "alkynyl" preferably denote $C_2$–$C_8$ hydrocarbon groups containing at least one double or triple bond, respectively.

The terms "lower alkyl", "lower alkoxy", "lower alkylthio", and "lower alkylsulfonyl" preferably denote functional groups in which the alkyl portion contains 1–6 carbon atoms.

The terms "substituted benzoxazol-2-yl" and "substituted benzothiazol-2-yl" refer to groups having the following formula

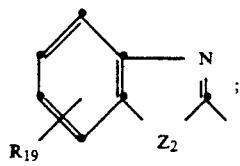

wherein $Z_2$ is —O— or —S—; $R_{19}$ is one or more lower alkyl, lower alkoxy, —O—lower alkylene—$CO_2R_{17}$, lower alkylene—$CO_2R_{17}$, halo, cyano, —$SO_2R_{16}$, —$NHCOR_{17}$, —$(R_{17})SO_2R_{16}$, —$CO_2R_{17}$, —$CON(R_{17})R_{18}$, or —$SO_2N(R_{17})R_{18}$ groups.

The term "substituted phenylene" preferably denotes a 1,2-, 1,3-, or 1,4-phenylene group substituted with one or more groups selected from the group consisting of lower alkoxy, halo, phenyl, hydroxy, and alkanoyloxy.

The term "substituted lower alkylene" refers to a straight or branched chain alkylene substituted by one or more lower alkoxy halogen, phenyl, hydroxy, or alkanoyloxy groups.

The new 4-aryl-3-heteroaryl-2(5H) furanone compounds (I) can be prepared by reacting 2-substituted intermediate acetophenones Ia with alkyl 2-(heteroalkyl) acetate esters (Ib) wherein X and Y

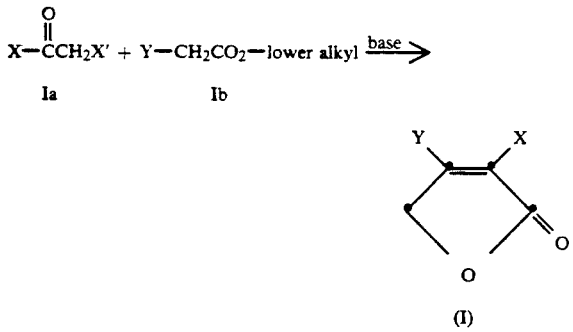

are defined above and X' is lower alkanoyloxy (preferably acetoxy). The reactions are conveniently carried out in lower alcohols in the presence of alkali metal hydroxides or alkoxides.

Methine UV/visible light absorbing compounds of Formulae (II) and (III) above can be prepared by reacting intermediate 2(5H) furanone active methylene compounds of Formula (I) above with a mono or bis carbocyclic or heterocyclic aldehyde, respectively. Usually the reactions are carried out under Knoevenagel reaction conditions. Bases such as piperidine, piperidine acetate, sodium acetate and pyridine are effective catalysts. Solvents such as alcohols, glycol ethers, N,N-dimethylformamide, N,N-dimethylacetamide and N-methyl-2-pyrrolidinone are convenient. Sometimes with the active methylenes of lesser reactivity, completion of the reaction may be facilitated by use of solvents or co-solvents such as refluxing benzene, toluene or xylene, whereby the water thus formed can be removed azeotropically as it is produced. Anhydrides, such as acetic anhydride, may also be used in some cases to effectively condense the aromatic aldehydes with the 2(5H) furanone active methylenes to produce the methine compounds. In this case, excess anhydride is normally used as the solvent. The intermediate aldehydes are prepared by well-established procedures, or are known already in the chemical literature.

As a further aspect of the present invention, there is provided a polyester composition having copolymerized therein or reacted therewith at least 0.001 weight percent of a residue of one or more light-absorbing compounds of formulae (II) and/or (III).

As a further aspect of the present invention, there is provided an amorphous color concentrate comprising an amorphous polyester having copolymerized therein or reacted therewith at least about 5.0 weight percent of a residue of a compound of Formulae (II) and/or (III).

As a further aspect of the present invention, there is provided a partially crystalline polyester color concentrate comprising a partially crystalline polyester having copolymerized therein or reacted therewith at least about 5.0 weight percent of a residue of a compound of Formula (II) and/or (III).

As a further aspect of the present invention, there is provided a colored semicrystalline powder having an average particle diameter of less than about 50 microns comprising a normally amorphous polyester or a partially crystalline polyester which has been modified by dissolution-crystallization-precipitation to impart increased crystallinity thereto having copolymerized therein or reacted therewith at least about 5.0 weight percent of a residue of a compound of Formula (II) and/or (III).

The colored polyester compositions provided by this invention comprise extrusion, molding and fiber grade, thermoplastic, linear polyester having reacted therewith or copolymerized therein a compound of Formula (II) and/or (III). It is apparent that the amount of residue present in the polyester material will vary substantially depending on several factors such as the particular compound being used, for example, the tint or depth of shade desired, and the thickness of the article, e.g., film, bottle, etc., to be produced from the colored polyester composition. For example, relatively thin film and thin-walled containers require higher levels of the compounds of Formula (II) and/or (III) to produce an equivalent color than do thicker articles such as sheet material or tubing.

The polyesters which may be used in the preparation of the compositions of our invention include linear, thermoplastic, crystalline or amorphous polyesters produced by conventional polymerization techniques from one or more diols and one or more dicarboxylic acids. The polyesters normally have an inherent viscosity (IV) of about 0.4 to about 1.2. The preferred polyesters comprise at least about 50 mole percent terephthalic and/or 2,6-naphthalenedicarboxylic acid residues and at least about 50 mole percent ethylene glycol and/or 1,4-cyclohexanedimethanol residues. Particularly preferred polyesters are those containing from about 75 to 100 mole percent terephthalic and/or 2,6-naphthalenedicarboxylic acid residues and from about 75 to 100 mole percent ethylene glycol residues.

The diol components of the described polyesters may be selected from ethylene glycol, 1,4-cyclohexane dimethanol, 1,2-propanediol, 1,3-propanediol, 1,4-butanediol, 2,2-dimethyl- 1,3-propanediol, 2-methyl-1,3-propanediol, 1,6-hexanediol, 1,2-cyclohexanediol, 1,4-cyclohexanediol, 1,2-cyclohexanedimethanol, 1,3-cyclohexanedimethanol, X,8-bis(hydroxymethyl)-tricyclo-[5.2.1.0]-decane wherein X represents 3,4, or 5; and diols containing one or more oxygen atoms in the chain, e.g., diethylene glycol, triethylene glycol, dipropylene glycol, tripropylene glycol and the like. In general, these diols contain 2 to 18, preferably 2 to 8 carbon atoms. Cycloaliphatic diols can be employed in their cis or trans configuration or as mixtures of both forms.

The acid components (aliphatic, alicyclic, or aromatic dicarboxylic acids) of the linear polyester are selected, for example, from terephthalic acid, isophthalic acid, 1,4-cyclohexanedicarboxylic acid, 1,3-cyclohexanedicarboxylic acid, succinic acid, glutaric acid, adipic acid, sebacic acid, 1,12-dodecanedioic acid, 2,6-naphthalenedioarboxylic acid and the like. In the polymer preparation, it is often preferable to use a functional acid derivative thereof such as the dimethyl, diethyl, or dipropyl ester of the dicarboxylic acid. The anhydrides or acid halides of these acids also may be employed where practical.

The novel light-absorbing polyester compositions provided by this invention are useful in the manufacture of containers or packages for comestibles such as beverages and foods. By the use of known heat setting techniques, certain of the polyesters are, in terms of color, I.V. and heat distortion, stable at temperatures up to about 100° C. Such stability characteristics are referred to as "hot-fill" stability. Articles molded from these polyesters exhibit good thin-wall rigidity, excellent clarity and good barrier properties with respect to moisture and atmospheric gases, particularly carbon dioxide and oxygen. The colored polyesters are particularly useful for the fabrication of containers having a wall thickness of about 10 to 30 mils. Further, the color concentrates of the present invention may be melt-blended with other colored or uncolored polyesters or blended with other polymers used in packaging materials. Thus, as a further aspect of the present invention, there is provided a formed article comprising the polyester composition as described above.

The linear polyesters most preferred for use in one embodiment of the invention comprise poly(ethylene terephthalate), poly(ethylene terephthalate) wherein up to 5 mole percent of the ethylene glycol residues have been replaced with residues derived from 1,4-cyclohexanedimethanol and poly(ethylene 2,6-naphthalenedicarboxylate) and wherein the polyesters have been sufficiently heat set and oriented by methods well known in the art to give a desired degree of crystallinity. For the manufacture of blow molded beverage bottles, the most preferred polyesters have an I.V. of 0.65 to 0.85, and a glass transition temperature (Tg) greater than 70° C. The glass transition temperature (Tg) referred to herein is determined by Differential Scanning Calorimetry at a scan rate of 20 Centigrade Degrees/minutes. The inherent viscosities (I.V., dL/g) of the polyesters described herein are determined at 25° C. using 0.5 g polymer per 100 mL of a solvent consisting of 60 parts by weight phenol and 40 parts by weight tetrachloroethane.

Compounds of Formulae (II) and/or (III) are preferably added at levels of about 1-5,000 ppm (parts by weight) before or during the polymerization reaction. For example, the compounds may be added along with the initial glycol and diacid (or ester) reactants, immediately prior to the polycondensation stage or subsequently. For this end use, the compounds of Formulae (II) and/or (III) may contain one or a multiplicity of reactive groups, since addition of the copolymerizable colorants in relatively low levels does not interfere substantially with the polymer preparation even if chain termination or cross linking do occur.

The compounds of Formula (II) and/or (III) and the reacted residues thereof possess the critical property of being sufficiently thermally stable to permit their copolymerization with polyesters by adding them at the start or at an early stage of the polyester preparation. Neither the above compounds nor their reacted residues sublime under polymerization conditions and the residues are not extractable from the polyesters. The thermal stability of the compounds of Formulae (II) and (III) are particularly important in the preparation of the light absorbing concentrates, i.e., polyesters containing from 1.0, especially at least 5.0, to as high as 50 weight percent of such residues. The light absorbing concentrates are advantageous in that the colorant moiety (1) is stable to light, heat and chemicals, (2) is resistant to sublimation, heat migration, bleeding and leaching by solvents, (3) possesses high color value or chroma and visible light absorption characteristics and/or UV absorbance which allows the light absorbing concentrates to be combined with other light absorbing concentrates to provide a range of colors and/or UV absorbers, (4) is safe to humans and the environment, and (5) may be blended with other polymers.

The amorphous light absorbing concentrates of our invention exhibit a glass transition temperature (Tg) and no, or only a trace of, crystallization or melting point by differential scanning calorimetry (DSC). Examples of such amorphous polyesters include those obtained by the polymerization of a compound of Formulae (II) and/or (III), terephthalic and/or 2,6-naphthalenedicarboxylic acid and a branched chain diol having the formula

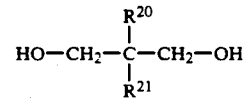

wherein $R^{20}$ is hydrogen or an unsubstituted or substituted alkyl, cycloalkyl or aryl radical, and $R^{21}$ is an unsubstituted or substituted alkyl, cycloalkyl or aryl radical. Preferred amorphous polyester light absorbing concentrates have an inherent viscosity of about 0.2 to 0.8 and are comprised of:
(i) diacid residues comprised of at least 50, preferably at least 80, mole percent terephthalic and/or 2,6-naphthalenedicarboxylic acid residues;
(ii) diol residues comprised of at least 50, preferably at least 80, mole percent of residues of a diol having the formula

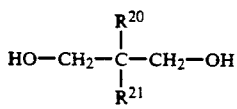

wherein $R^{20}$ is hydrogen or lower alkyl and $R^{21}$ is lower alkyl; and (iii) residues of a light absorbing compound of Formulae (II) and/or (III).

The particularly preferred amorphous polyester light absorbing concentrates are comprised of (i) diacid residues consisting essentially of terephthalic and/or 2,6-naphthalenedicarboxylic acid residues; (ii) diol residues consisting essentially of 2,2-dimethyl-1,3-propanediol residues; and (iii) residues of a compound of Formula (II) and/or (III).

Other amorphous polyesters, as defined above, suitable for preparing the light absorbing semicrystalline powders may be obtained by employing (1) two dicarboxylic acids and one or more diols or (2) two diols and one or more dicarboxylic acids according to known procedures for obtaining amorphous polyesters. The polyester comprising a diacid component consisting of 75 mole percent terephthalic acid residues and 25 mole percent 1,4-cyclohexanedicarboxylic acid residues, a diol component consisting of 1,4-butanediol residues and residues of a compound of Formula (II) is an example of such a polyester.

The partially-crystalline color concentrates of this invention usually exhibit a glass transition temperature, a crystallization temperature and a melting temperature by DSC. These partially-crystalline, polyester concentrates are comprised of (i) diacid residues consisting of at least 80 mole percent terephthalic acid residues, 2,6-naphthalenedicarboxylic acid residues, 1,3-zyclohexanedicarboxylic acid residues, 1,4-cyclohexanedicarboxylic acid residues or a mixture thereof, (ii) diol residues consisting of at least 50 mole percent of residues having the formula $-O-(CH_2)_p-O-$ wherein p is 2, preferably 4, to 12 and (iii) residues of colorant compound (II) and/or (III). A preferred partially-crystalline color concentrate has a melting temperature of at least 110° C. and is comprised of (i) diacid residues comprised of at least 80 mole percent terephthalic acid residues, (ii) diol residues comprised of at least 80 mole percent of residues of 1,4-butanediol and (iii) residues of a colorant compound of Formula (II). An especially preferred partially-crystalline color concentrate has a melting temperature of at least 110° C. and consists essentially of (i) terephthalic acid residues, (ii) 1,4-butanediol residues and (iii) a colorant compound of Formula (II).

The light absorbing semicrystalline powders provided by this invention may be obtained by means of a dissolution-crystallization-precipitation procedure wherein the amorphous or partially-crystalline polyester color concentrates described above are dissolved in an organic solvent from which the polymeric color concentrate is recovered in a finely divided form consisting of particles of relatively uniform size, e.g., from about 10 to 50 microns. If desired, the particle size of the colored semicrystalline powders may be reduced further by conventional grinding processes. Examples of solvents in which the amorphous and/or partially-crystalline concentrates may be dissolved include halogenated hydrocarbons such as aliphatic chlorides, e.g., methylene chloride; esters such as alkyl esters of carboxylic acids, e.g., ethyl acetate and methyl benzoate; hydrocarbons such as toluene; and ethers such as tetrahydrofuran. We have found methylene chloride to be a particularly effective solvent.

The particular dissolution-crystallization-precipitation procedure utilized is not critical. The amorphous or partially crystalline concentrate may be dissolved in a suitable solvent at elevated temperatures and then crystallized in a finely-divided state by cooling, with or without a reduction in the volume of solvent, i.e., either with or without a solution concentration step. Another useful technique involves dissolving the amorphous concentrate in an organic solvent, either at ambient or elevated temperature, and then adding to the solution another miscible solvent which causes crystallization of the colored semi-crystalline powder. The use of methylene chloride as the primary solvent and an alkyl acetate such as ethyl acetate as the "crystallization-inducing" solvent has been found to be particularly efficacious. Depending on their intended utility, the colored semicrystalline powders may be extracted with a suitable organic solvent to remove relatively low molecular weight polyester oligomers. Examples of oligomer-extracting solvents include ketones such as acetone, 2-pentanone, 3-methyl-2-butanone, 4-methyl-2-pentanone, 2-hexanone and 5-methyl-2-hexanone; hydrocarbons such as hexane, heptane and toluene; and ethers such as tetrahydrofuran. Another, but not preferred, dissolution-precipitation procedure involves dissolving the amorphous color concentrates in certain solvents, e.g., ethyl acetate, from which the polymeric light absorbing concentrate, after undergoing a change in morphology, precipitates.

Some of the more crystalline polyesters such as poly(ethylene terephthalate) and poly(tetramethylene terephthalate) require the use of a high-boiling solvent in the dissolution-precipitation procedure. Examples of such high-boiling solvents include alkyl esters of aromatic carboxylic acids, e.g., alkyl benzoates, and alkyl phthalates; aliphatic dicarboxylic acid esters; glycol esters, e.g., ethylene glycol diacetate; diethylene glycol diacetate; aromatic ketones, e.g., acetophenone, and aromatic oxides; e.g., diphenyl oxide; and aliphatic carboxamides, e.g., N,N-dimethylformamide and isophorone. Methyl benzoate and ethylene glycol diacetate are particularly preferred high-boiling solvents since they are readily available, have a pleasant odor and do not cause color problems during crystallization which sometimes is a problem with acetophenone.

In one variation of the process, crude polyester light absorbing concentrate is prepared and granulated to a very course powder which is heated with a high-boiling solvent (methyl benzoate) to facilitate solution. Upon cooling, crystallization-precipitation occurs and a diluent such as acetone usually is needed to permit stirring. Filtration gives the finely-divided powder which may require washing or reslurrying to remove the crystallization solvent.

In another variation of the dissolution-crystallization-precipitation process, crystallization can occur as an integral part of the polyester color concentrate manufacturing process wherein the crystallization solvent is added to a melt of the concentrate to obtain a solution of the color concentrate which then may be obtained as a powder by precipitation. The polyester light absorbing concentrate powder is thus obtained in a purified form without the need of granulating by a means which may be used in conjunction with batch processing.

The dissolution-crystallization-precipitation procedure alters the morphology of the amorphous and partially-crystalline polyester light absorbing concentrates in a number of respects. X-Ray diffraction analysis of the colored semicrystalline powders shows a marked increase in the crystallinity of the polyester and, while the amorphous polyester concentrates do not exhibit a melting temperature, the microcrystalline concentrates usually (almost always) exhibit a melting temperature by DSC. Although the weight average molecular weight (Mw) may increase, decrease or not be changed by the dissolution-crystallization-precipitation procedure, the number average molecular weight (Mn) always increases, the magnitude of the increase depending on the degree to which oligomeric material has been removed from the colored semicrystalline polyester powder. The polydispersity ratio (Mw:Mn) of the colored semicrystalline polyester is always less than that of the polyester concentrate from which it is prepared due to the increase in Mn (even when Mw increases, Mn increases more). Finally, the inherent viscosity of the colored semicrystalline powders normally is slightly higher than that of the color concentrate.

The amorphous and partially-crystalline polyester light absorbing concentrates may be used in coloring and/or imparting UV absorbing various thermoplastic polymeric materials when non-extractability or non-volatility of the colorant is critical because of toxicity considerations, e.g., in rigid and flexible packaging materials for food. The concentrates and powders may be used in formulating inks, coatings, toners for impactless printing, and similar products.

The polyester light absorbing concentrates may be prepared according to conventional esterification or transesterification and melt polycondensation procedures using (i) a dicarboxylic acid or, preferably, a lower alkyl ester thereof, (ii) a diol and (iii) a compound of Formula (I) bearing one to four, preferably about two, polyester reactive groups. Normally, at a 50 mole percent excess of the diol is used. The compound of Formula (II) and/or (III) preferably is added with the other monomers at the commencement of the concentrate manufacture although it may be added subsequently, e.g., at the beginning or during the polycondensation step. The concentration (weight percent) of the residue is determined by summing up the weights of all the components charged to the reactor and subtracting the sum of the weights of the components removed during transesterification and polycondensation, e.g., methanol and excess diol. The difference represents the theoretical yield of the color concentrate. The weight of the compound of formulae (II) and/or (III) charged to the reactor is divided by the theoretical weight and multiplied by 100 to give the weight percent of the residue of formulae (II) and/or (III).

As a further aspect of the present invention, there is provided a light-absorbing thermoplastic polymer composition, which comprises one or more thermoplastic polymers and one or more colored polyester compositions of the present invention.

The thermoplastic resin systems useful for blending with the light absorbing polyester compositions of the present invention include polyesters such as poly(ethylene terephthalate); polyamides such as nylon 6 and nylon 66; polyimides, polyolefins, e.g., polyethylene, polypropylene, polybutylene and copolymers made from ethylene, propylene or butylene. Other thermoplastic polymers include cellulosic resins such as cellulose acetate, cellulose propionate, or cellulose butyrate; polyacrylate resins such as polymethyl methacrylate; polycarbonates; polyurethanes; polystyrene; polyacrylonitrile; polyvinylidene chloride; polyvinyl chloride, etc.

Colorants having the Formulae II and III above also have utility as disperse dyes for polyester fibers and have a high degree of pH stability and excellent sublimation fastness when applied as colorants to polyester fibers as disperse dyes.

Experimental Section

Example 1—Preparation of 2—Acetoxyacetophenone

A mixture of 2-bromoacetophenone (199 g, 1.0M), acetic acid (200 mL) and acetic anhydride (30 mL) was stirred and heated to about 60° C. Anhydrous sodium acetate (100 g, 1.2M) was added and the reaction mixture was heated and stirred at about 130° C. for 6.0 hrs and then allowed to cool. To remove most of the salt, the reaction mixture was filtered through a sintered glass funnel. The acetic acid and acetic anhydride were removed from the filtrate using a rotary evaporator. A white solid was obtained upon cooling (yield—97.0 g). Mass spectroscopy supported the proposed structure.

Example 2—Preparation of Ethyl α-Benzoxazol- 2-yl Acetate

Ethyl 3-ethoxy-3-iminopropionate HCl.[CH$_2$H$_5$OC(=NH)—CH$_2$CO$_2$C$_2$H$_5$. HCl] (195.5 g, 1.0M) was dissolved in methanol (750 mL) by stirring and the solution cooled to about 15° C. To this solution was added 2-aminophenol portionwise over about 20 minutes. The reaction mixture was stirred at room temperature for about 20 hours and then filtered to remove the salt. Upon addition of cold water (875 mL) to the stirred filtrate, the white product crystallized and was collected by filtration, washed with water and dried in air. The product was recrystallized from methanol in the presence of charcoal to yield 125 g (61% of the theoretical yield) of product which melted at 51° C. Mass spectrometry supported the following desired structure.

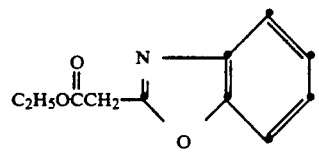

Example 3—Preparation of Ethyl α-(Benzothiazol-2-yl) Acetate

To ethyl 3-ethoxy-3-iminopropionate.HCl (39.1 g, 0.20M) dissolved in methanol (50 mL) was added 2-aminobenzenethiol (25.0 g, 0.20M) at room temperature with stirring. After being stirred at room temperature for 20 hours, the reaction mixture was filtered to remove the salt. To the filtrate was added water (250 mL) and methylene chloride (50 mL). After the mixture was shaken in a separatory funnel the organic layer was recovered and the solvent removed therefrom using a rotary evaporator. The oily, slightly yellow product thus obtained weighed 44.0 g (99.5% of the theoretical yield) and had the following structure as evidenced by mass spectrometry:

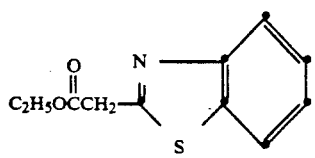

Example 4—Preparation of Ethyl α-(5-Carbomethoxybenzoxazol-2-yl) Acetate

To ethyl 3-ethoxy-3-iminopropionate.HCl (156 g, 0.80M) in methanol (640 mL) was added methyl 3-amino-4-hydroxybenzoate (133.6 g, 0.80M) with stirring and the reaction mixture was heated at reflux for 7 hours. Additional methanol (500 mL) and ethyl 3-ethoxy-3-iminopropionate.HCl (20 g) were added and the reaction mixture was heated an additional 17 hours at reflux and then drowned into water (1.5 L). The product thus produced was initially oily but crystallized after standing several hours at room temperature. The water was removed and the product washed with fresh water by decantation. Recrystallization of the water wet solid from methanol (300 mL) gave 127.6 g of product (60.7% of the theoretical yield). Mass spectrometry supported the following desired structure:

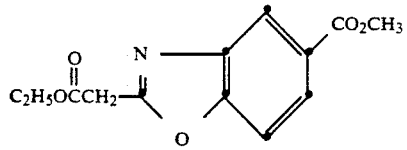

Example 5—Preparation of 3-(Benzoxazol-2-yl)-4-Phenyl-2-(5H) Furanone

To a stirred solution of 2-acetoxyacetophenone (from Example 1) (8.9 g, 0.05M) and ethyl α(benzoxazol-2-yl) acetate (from Example 2) (10.2 g, 0.05M) dissolved in methanol (40 mL) was added a solution of sodium hydroxide (2.5 g) dissolved in methanol (30 mL). A slight exotherm occurred and the reaction mixture was stirred at about room temperature for 1.0 hour (Note: longer times resulted in poorer quality product). Concentrated HCl was added dropwise with good stirring to adjust the pH to about 5.0 and the reaction mixture was cooled to about 15° C. The greenish-yellow product thus produced was collected by filtration and dried in air (yield—8.4 g, 61% of the theoretical yield). The compound absorbs ultra-violet light strongly at 310 nm (εmax-9,397) and 278 nm (εmax-8,981) in methylene chloride/methanol (85.0/15.0 by volume). Mass spectrometry supports the following structure:

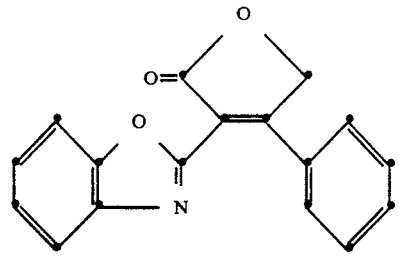

Example 6—Preparation of 3-(5-Carbomethoxybenzoxazol-2-yl)-4-Phenyl-2-(5H) Furanone A solution was prepared by dissolving ethyl α-(5-carbomethoxybenzoxazol-2-yl) acetate (52.6 g, 0.20M) (from Example 4) and 2-acetoxyacetophenone (35.6 g, 0.20M) (from Example 1) in methanol (200 mL) by stirring at room temperature. To this solution was added at room temperature a solution prepared by dissolving sodium hydroxide pellets (18.0 g, 0.45M) in methanol (120 mL). The product precipitated almost immediately and a slight exotherm was observed. After being stirred about 2.0 hours longer, with no external heating, the reaction mixture was drowned into water (1.6 L) and then concentrated HCl was added with stirring until a pH of 4-5 was observed. The pale greenish yellow solid was collected by filtration, washed with water and dried in air (yield 66.4 g, 99.1% of the theoretical yield). Under long wavelength UV light, a strong greenish yellow fluorescence was observed. Mass spectrometry supported the following structure:

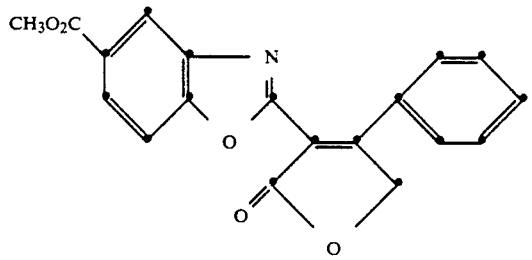

Absorption maxima were observed at 289 nm (εmax—7,124) and 314 nm (6max—7,531) in the UV light absorption spectrum in methylene chloride.

Example 7—Preparation of 3-(Benzothiazol- 2-yl)-4-Phenyl-2-(5H) Furanone

A solution of 2-acetoxyacetophenone (from Example 1) (8.9 g, 0.05M) and α-(benzothiazol-2-yl)-acetate (from Example 3) dissolved in methanol (40 mL) by stirring at room temperature was treated at room temperature with a solution prepared by dissolving sodium hydroxide pellets (2.5 g) in methanol (30 mL) by stirring. A slight exothermic reaction was observed. After being stirred at about room temperature for about 1.0 hour, the reaction mixture was acidified to a pH of about 4 by the dropwise addition of concentrated HCl. The product which was a dark brown colored semi-crystalline mass was washed by decantation and dried in air (yield—12.0 g (81.9% of the theoretical yield). Mass spectrometry indicated that the product largely consisted of the following desired compound:

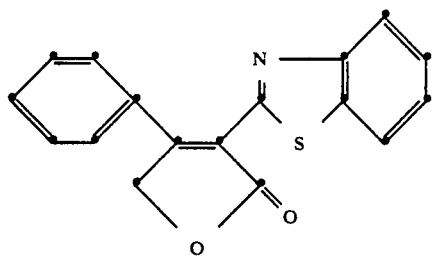

In the UV light absorption spectrum in methylene chloride, absorption maxima were observed at 298 nm ($\epsilon$max—5,585) and 353 nm ($\epsilon$max—5,636).

Example 8—Preparation of Ethyl α[[5(6)-Methylsulfonyl]-Benzoxazol-2-yl] Acetate A mixture of 2-amino4-methylsulfonylphenol (4.67 g, 0.025M) and 2-amino-5-methylsulfonylphenol (4.67 g, 0.025M) was dissolved by warming in methanol (50.0 mL) with stirring. The solution was allowed to cool to room temperature and heptane wet ethyl 3-ethoxy-3-iminopropionate.HCl [$C_2H_5OC(C=NH)$—$CH_2CO_2C_2H_5$.HCl] (0.05M) was added and the reaction mixture stirred at room temperature for 20 hours. Water (50 mL) was added and the product was extracted into methylene chloride (50 mL) using a separatory funnel. Solvent was removed from the organic layer to yield a pale orange liquid product which solidified upon standing at room temperature overnight (yield—8.2 g). Mass spectrometry showed that the product had the desired molecular weight (283) and thin layer chromatography showed two UV absorbing products present. It was proposed that the product was an isomeric mixture of I and II.

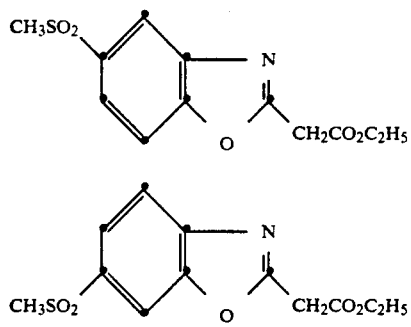

Example 9—Preparation of 3-[5(6)-Benzoxazol-2-yl]-4-Phenyl-2-(5H) Furanone

The product of Example 8 (7.08 g, 0.025M) and the ω-acetoxyacetophenone (4.45 g, 0.025M) of Example 1 were dissolved by stirring and warming in methanol (20 mL). This solution was then added to a solution of sodium hydroxide (1.3 g) dissolved in methanol (15 mL). Stirring was continued for one hour at about room temperature. Water (50 mL) was added and the reaction mixture was acidified to pH of about 5 by addition of conc. HCl. The resulting product separated as a soft dark yellow mass and was washed twice with water by decantation and then allowed to dry in air (yield—4.3 g, 48.4% of the theoretical yield). The product hardened upon standing at room temperature. Mass spectrometry indicated that the material had the desired molecular weight (355) and colorants prepared therefrom showed two components by thin layer chromatography. Thus, it was concluded that the reaction product was a mixture of isomers, III and IV.

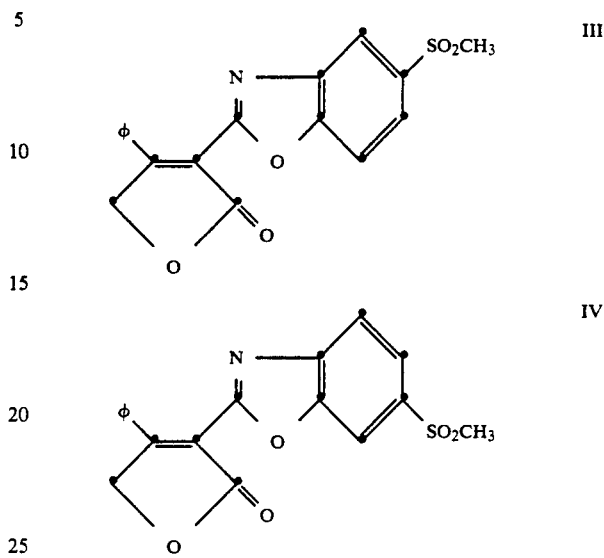

Example 10—Preparation of Ethyl α-(5-Sulfamoylbenzoxazol-2-yl) Acetate

A solution was prepared by dissolving 2-amino-4-sulfamoylphenol (18.8 g, 0.10M) in methanol (100 mL) by stirring and warming. The solution was allowed to cool and heptane wet ethyl 3-ethoxy-3-iminopropionate.HCl [$C_2H_5$—$C(=NH)$—$CH_2CO_2C_2H_5$.HCl] (0.10M) was added and stirring continued for 20 hours. Additional methanol (50 mL) was added to facilitate stirring during the course of the reaction. The reaction mixture was filtered and the white product washed with methanol and dried in air (yield—14.6 g, 51.4% of the theoretical yield; m.p. 163°-165° C.). Mass spectrometry supported the following structure:

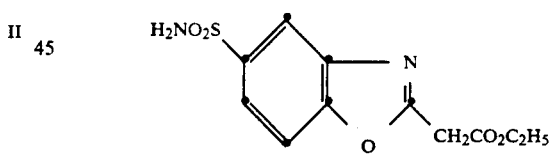

Example 11—Preparation of 4-Phenyl-3-(5-Sulfamoylbenzoxazol-2-yl)-2(5H) Furanone A slurry of ethyl α-(5-sulfamoylbenzoxazol-2-yl) acetate (11.36 g, 0.04M) from Example 10 and ω-acetoxyacetophenone (7.12 g, 0.04M) from Example 1 in methanol (150 mL) was added with stirring to a solution of sodium hydroxide (2.5 g) dissolved in methanol (30 mL). Stirring was continued for 1 hour and a dark yellow solution resulted. The reaction solution was drowned into water (200 mL) and the resulting mixture was acidified by adding conc. HCl to pH of approximately 5. The dark yellow solid was collected by filtration, washed with water and dried in air (yield 6.81 g). A second crop of product (1.75 g) was recovered by refiltration of the original filtrate. Mass spectrometry showed both crops of product to be of about equal purity and to be mostly the desired product, having a molecular weight of 356. The proposed structure is as follows:

ethanol (20 mL) and piperidine (10 drops) was treated as in Example 12 and the product (1.18 g, 50.6% of the theoretical yield) isolated similarly. Mass spectrometry supports the following desired structure:

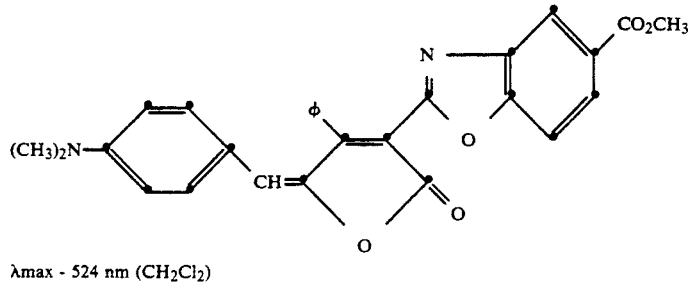

λmax - 524 nm (CH₂Cl₂)

In the visible absorption spectrum in methylene chloride a λmax was observed at 524 nm (ε=49,033).

Example 14

4-(Dimethylamino)benzaldehyde (0.75 g, 0.005M) was reacted with 3-(benzothiazol-2-yl)-4-phenyl-2-(5H) furanone (1.46 g, 0.005M) from Example 7 in ethanol (15 mL) and and the presence of piperidine acetate (6 drops) by heating and stirring at reflux for 1 hour. The reaction mixture was filtered hot and the product washed with ethanol and dried in air. A yield of 0.63 g (29.7% of the theoretical yield) was obtained of product having the following structure as evidenced by mass spectrometry:

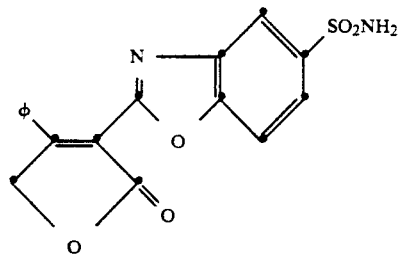

Example 12

A reaction mixture of 4-(dimethylamino) benzaldehyde (0.30 g, 0.002M), 3-benzoxazol-2-yl)-4-phenyl-2-(5H) furanone (0.55 g, 0.002M) from Example 5, ethanol (10 mL) and piperidine (6 drops) was heated at reflux for 1 hour, during which time the product crystallized. The reaction mixture was allowed to cool. Filtration, followed by washing the solid with methanol, and drying in air yielded 0.56 g (68.6 % of the theoretical yield) of bright red crystalline product. Mass spectrometry supported the following desired structure:

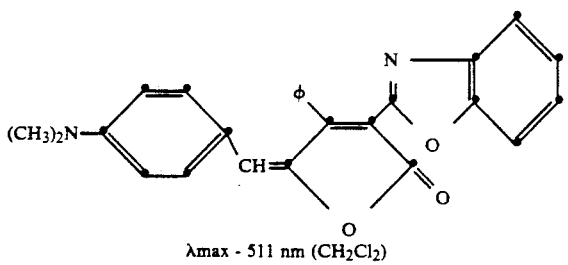

λmax - 511 nm (CH₂Cl₂)

In the visible absorption spectrum in methylene chloride an absorption maximum (λmax) was observed at 511 nm [extinction coefficient (ε)=35,876].

Example 13

A mixture of 3-(5-carbomethoxybenzoxazol-2-yl)-4-phenyl-2-(5H) furanone (1.67 g, 0.005M) from Example 6, 4-(dimethylamino)benzaldehyde (0.75 g (0.005M),

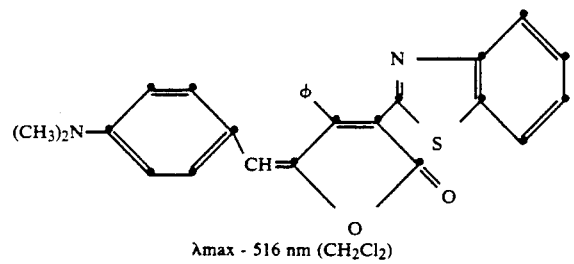

λmax - 516 nm (CH₂Cl₂)

In the visible absorption spectrum in methylene chloride a λmax was observed at 516 nm (ε=30,329).

Example 15

A reaction mixture of 4-[N-2-(acetoxylethyl)-N-ethyl)amino]-o-tolualdehyde (18.7 g, 0.075 m), 3-(5-carbomethoxybenzoxazol-2-yl)-4-phenyl-2-(5H) furanone (25.1 g, 0.075M) from Example 6, isopropanol (225 mL) and sodium acetate (7.5 g) was heated with stirring at reflux for 1 hour. The heat was removed and methanol (250 mL) was added to the reaction mixture and the product crystallized by cooling, collected by filtration, washed with methanol (200 mL) and dried in air. The yield was 20.5 g (48.3% of the theoretical yield) of dark red solid which had the following structure as evidenced by mass spectrometry:

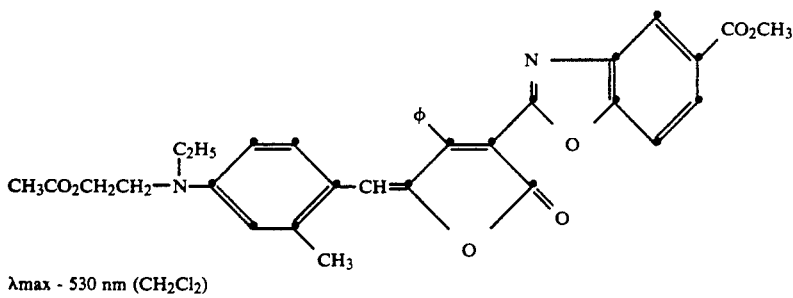

λmax - 530 nm (CH₂Cl₂)

An absorption maximum (λmax) was observed at 530 nm in methylene chloride ($\epsilon=34{,}574$).

Example 16

4-[N-2-(acetoxyethyl)-N-ethylamino] benzaldehyde (11.75 g, 0.05M) was reacted with 3-(5-carbomethoxybenzoxazol-2-yl)-4-phenyl-2-(5H) furanone (16.75 g, 0.05M) by heating and stirring in isopropanol (150 mL) in the presence of sodium acetate (5.0 g) for 1 hour at reflux. Some of the red product crystallized during the last part of the heating period. The cooled reaction mixture was filtered and the dark red solid was collected by filtration, washed with methanol and dried in air (yield—14.6 g, 54.8% of the theoretical yield). Mass spectrometry supports the following structure:

while still moist. The mixture was cooled and the product collected by filtration, washed with ethanol and dried in air (yield 0.44 g). Mass spectrometry indicated some of V, containing the free carboxylic acid group present, but appeared to be mostly VI, the anhydride.

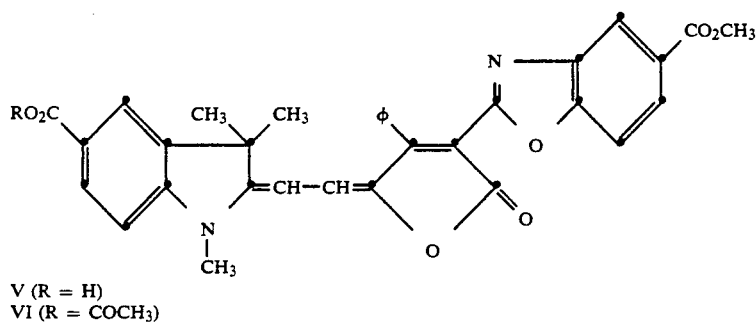

V (R = H)
VI (R = COCH₃)

In the visible spectrum in methylene chloride, a λmax at 563 nm was observed. Based on the molecular weight of VI (604.6) an extinction coefficient of 54,666 was calculated.

Example 18

A reaction mixture of 5-carboxy-1,3-dihydro-1,3,3-trimethyl-2H-indol-2-ylideneacetaldehyde (1.23 g, 0.005M), 3-benzothiazol-2-yl-4-phenyl-2-(5H) furanone (1.47 g, 0.005M) and acetic anhydride was heated at

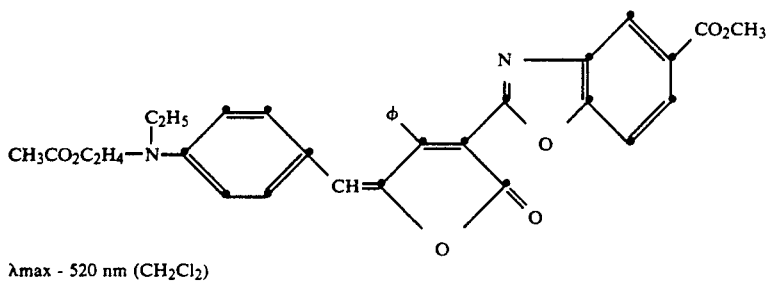

λmax - 520 nm (CH₂Cl₂)

In the visible absorption spectrum a λmax is observed at 520 nm ($\epsilon=39{,}873$).

Example 17

A reaction mixture of 5-carboxy-1,3-dihydro-1,3,3-trimethyl-2H-indol-2-ylideneacetaldehyde (0.49 g, 0.002M), 3-(5-carbomethoxy-2-benzoxazol-2-yl)-4-phenyl-2-(5H) furanone, acetic anhydride (10 mL) was heated at 90 95° C. with stirring for 1 hour and then drowned into water. After 2-3 hours a red solid resulted as the excess anhydride hydrolyzed. The product was collected by filtration and reslurried in hot ethanol 90°-95° C. for 1.5 hours and then drowned into warm water (150 mL). After standing several hours at room temperature, the aqueous layer was removed by decantation. The heavy red oil was treated with ethanol and the mixture heated to reflux to dissolve the product. Upon cooling the red colorant crystallized and was collected by filtration, washed with ethanol and dried in air (yield—0.48 g). Mass spectrometry and thin layer chromatography showed a three component mixture likely corresponding to VII, VIII and IX, with VII being the major component.

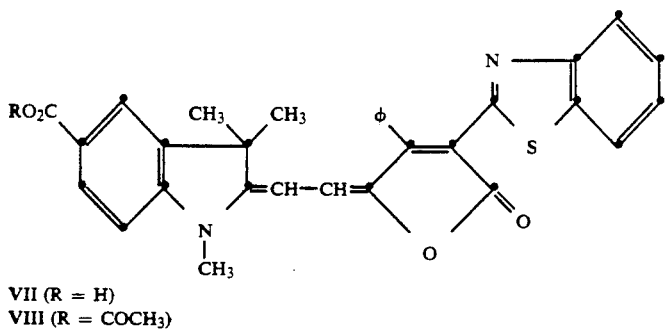

VII (R = H)
VIII (R = COCH₃)

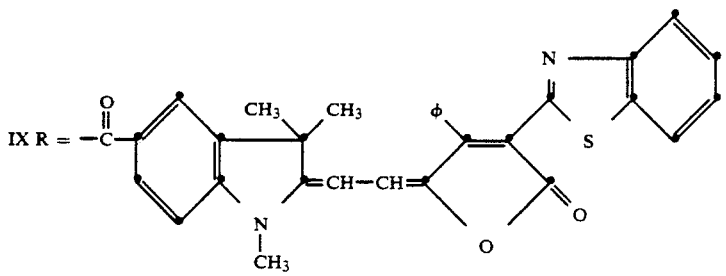

IX R = —C(=O)—

An absorption maximum was observed at 538 nm in methylene chloride.

Example 19

A reaction mixture of 4[[N-(4-carbomethoxyphenylmethyl)-N-ethyl]amino]-o-tolualdehyde (18.4 g, 0.055M), 3-(5-carbomethoxy-benzoxazol-2-yl)-4-phenyl-2-(5H) furanone (17.1 g, 0.055M), ethanol (250 mL) and piperidine acetate (1.5 g) was heated and stirred at reflux for 1 hour and then allowed to cool. The dark red solid was collected by filtration, washed with ethanol and dried in air (yield—17.4 g, 50.4% of the theoretical yield). Mass spectrometry supported the following structure:

In the visible absorption spectrum a λmax was observed at 526 nm in methylene chloride (ε=34,962).

Example 20

A reaction mixture of N-(2-acetoxyethyl)-2,5-dimethyl-6-formyl-8-methoxy-1,2,3,4-tetrahydroquinoline, 3-benzothiazol-2-yl)-4-phenyl-2-(5H) furanone (1.46 g, 0.005M) from Example 7, ethanol (20 mL) and piperidine (6 drops) was heated and stirred at reflux for 1 hour, filtered hot to remove a few insoluble particles and allowed to cool. The dark red solid was collected by filtration, washed with ethanol and dried in air (yield—0.3 g, 10.3% of the theoretical yield). Mass spectrometry supports the following structure:

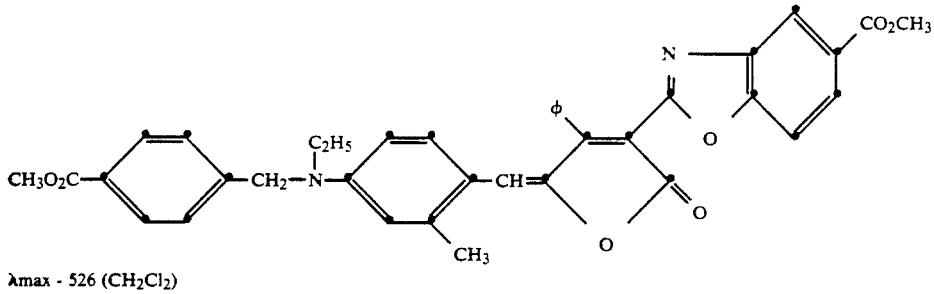

λmax - 526 (CH₂Cl₂)

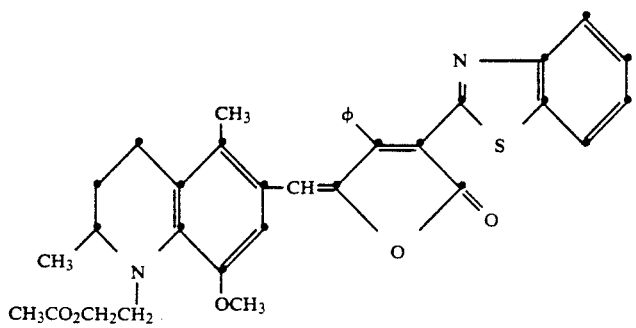

λmax - 516 nm

An absorption maximum at 516 nm (ε=71,085) in the visible absorption spectrum in methylene chloride.

Example 21

4-[2-(Hydroxyethoxy)]-3-methoxybenzaldehyde (0.49g, 0.0025M), 3-(5-carbomethoxybenzoxazol-2-yl)-2-(5H) furanone (0.84 g, 0.0025M), ethanol (10 mL) and piperidine (5 drops) were heated and stirred at reflux for 1 hour. The reaction mixture was allowed to cool and the golden yellow solid was collected by filtration, washed with ethanol and dried in air (yield—0.60 g, 46.9% of the theoretical yield). Mass spectrometry supports the following desired product:

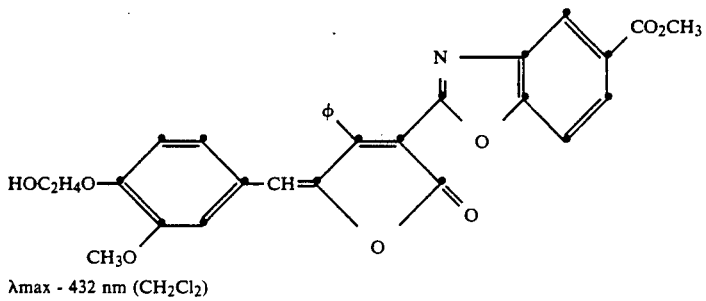

λmax - 432 nm (CH₂Cl₂)

In the visible absorption spectrum in methylene chloride a λmax was observed at 432 nm (ε—34,918).

Example 22

A reaction mixture of 4,4'-[(1,2-ethanediyl)bis-(oxy)-bis(3-methoxybenzaldehyde (0.33 g, 0.001M), 3-(5-carbomethoxybenzoxazol-2-yl)-4-phenyl-2-(5H) furanone (0.67 g, 0.002M) from Example 6, N,N-dimethylformamide (10 mL) and piperidine (5 drops) was heated at about 95° C. for 2.0 hours with occasional stirring, during which time the yellow product crystallized, and then drowned into acetone (50 mL). Filtration, washing with acetone and drying in air yielded 0.38 g of product. Mass spectrometry and thin layer chromatography indicated mostly the desired bis compound X, but with some mono compound XI also present.

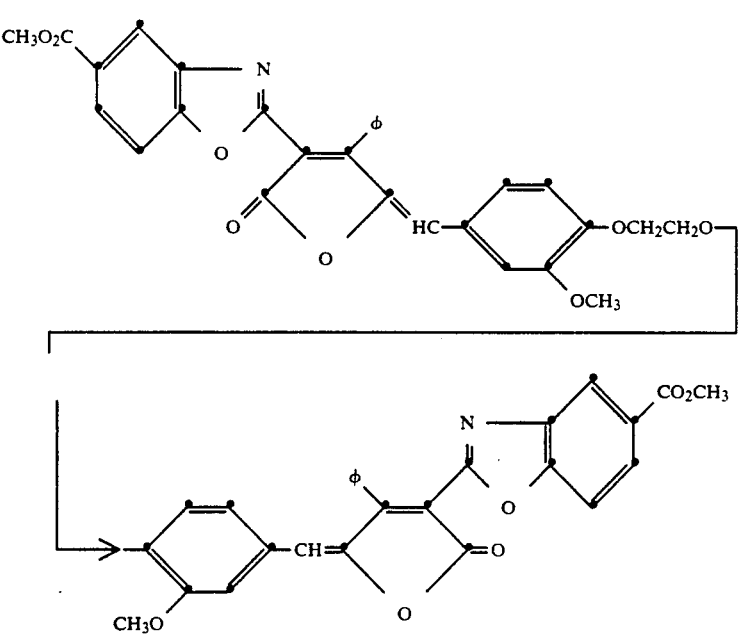

X

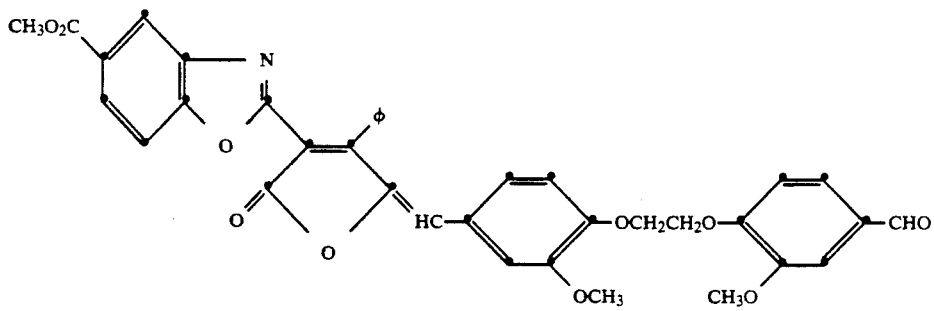

XI

An absorption maximum was observed at 439 nm in the visible absorption spectrum in methylene chloride.

Example 23

2-Furaldehyde (0.48 g, 0.005M) was reacted with 3-(5-carbomethoxybenzoxazol-2-yl)-4-phenyl-2-(5H) furanone (1.67 g, 0.005M) in methanol in the presence of 6 drops of piperidine by heating and stirring the reaction mixture for 1.0 hour. After cooling, the reaction mixture was filtered and the yellow product washed with methanol and dried in air (yield—1.02 g, 49.3% of the theoretical yield). Mass spectrometry supports the following desired structure:

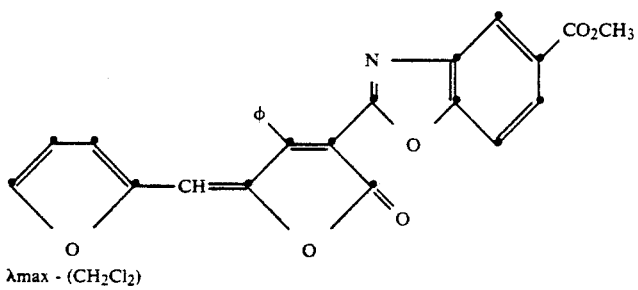

$\lambda$max - (CH$_2$Cl$_2$)

In the visible absorption spectrum in N,N-dimethylformamide a $\lambda$max is observed at 425 nm ($\epsilon$=41,216).

Example 24

The following bis aldehyde (1.09g, 0.002M)

was reacted with 3-(5-carbomethoxybenzoxazol-2-yl)-4-phenyl-2-(5H) furanone (1.47 g, 0.0044M) in N,N-dimethylformamide in the presence of piperidine (6 drops) by heating at 90°-95° C. for 2.0 hours with stirring. The reaction mixture was drowned into methanol (100 mL) with stirring and the solid product (yield—0.82 g) was collected by filtration, washed with methanol and dried in air. Thin-layer chromatography and mass spectral analysis showed a mixture of desired bis product and half reacted mono product.

Example 25

A reaction mixture of p-hydroxybenzaldehyde (0.37 g, 0.003M), 3-(5-carbomethoxybenzoxazol-2-yl)-4-phenyl-2(5H) furanone (1.00 g, 0.003M), methanol (20 mL) and piperidine (6 drops) was heated and stirred at reflux for 1 hour and allowed to cool. The pH was adjusted to about 5-6 by dropwise addition of conc. HCl. After being stirred for 5 minutes the reaction mixture was filtered and the product washed with methanol and dried in air (yield—0.65 g, 49.2% of the theoretical yield). Mass spectrometry supported the following structure:

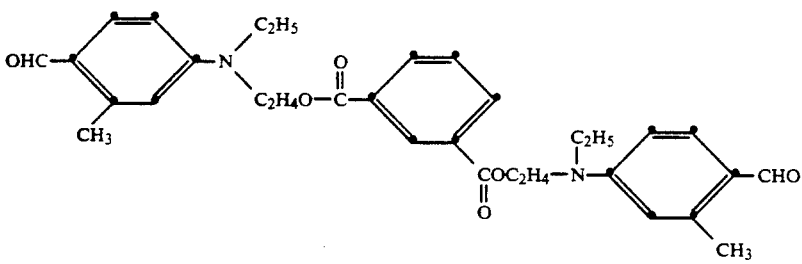

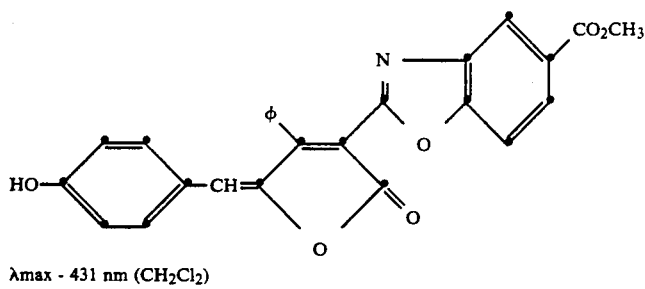

λmax - 431 nm (CH₂Cl₂)

In the visible absorption spectrum in N,N-dimethylformamide, an absorption maximum was observed at 431 nm ($\epsilon=36,021$).

Examples 26-37 (See Table 2)

The aromatic aldehyde (0.005M) was reacted with 3-(5-carbomethoxybenzoxazol-2-yl)-4-phenyl-2-(5H)furanone (0.005M) in methanol solvent in the presence of piperidine (6 drops) exactly as described in Example 23 and the products isolated similarly. Mass spectrometry was used to confirm the structure of the products. The UV/visible absorption spectra were all run using methylene chloride as the solvent.

Example 38

4-(Dimethylamino)cinnamaldehyde (0.88 g, 0.005M), 3-(5-carbomethoxybenzoxazol-2-yl)-4-phenyl-2-(5H)furanone (1.67 g, 0.005M), methanol (25 mL) and piperidine (6 drops) were mixed and heated with stirring for 1.5 hours. The solid product which resulted was collected by filtration, washed with methanol and dried in air (yield—0.6 g). Thin layer chromatography, using aluminum sheets precoated with silica gel and developing with acetone: n-hexane (10:90) showed two colorants present, one violet and the other one red. Mass spectrometry showed two components, one the desired structure XII and another compound having a molecular weight of 466.

the redder (hypsochromic) colorant had structure XIII. The product had a visible absorption maximum at 523 nm in methylene chloride.

Example 39

A reaction mixture of 2,2'-[(1,2-ethanediyl)bis-(oxy)]bis [benzaldehyde] (0.54 g, 0.002M), 3-(5-carbomethoxybenzoxazol-2-yl)-4-phenyl-2-(5H)furanone (1.34 g, 0.004M), N,N-dimethylformamide (15 mL) and piperidine (6 drops) was heated with stirring at 90°-95° C. for 1 hour and allowed to cool. The bright yellow solid was collected by filtration, washed with methanol and dried in air (yield—0.58 g). Mass spectrometry and thin layer chromatography showed mostly the desired bis-compound XIV, but also some of the half reacted compound XV present.

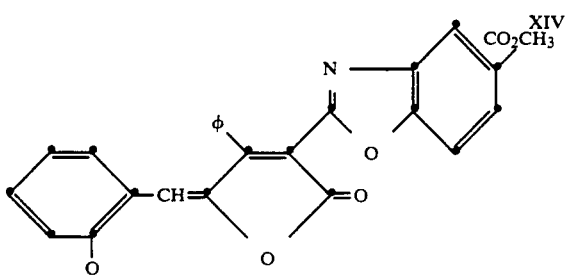

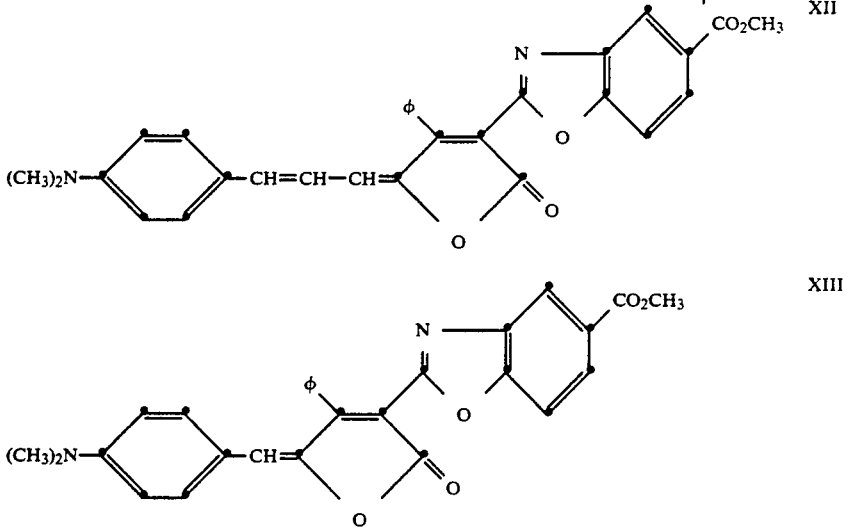

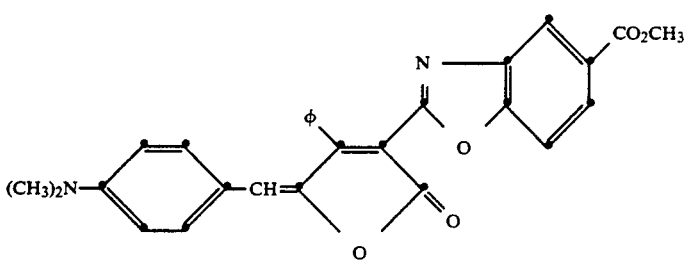

A known sample of the colorant of Example 13 matched the red component by thin layer chromatography and the molecular weight is identical. It was concluded that the violet component had structure XII and -continued 2-(5H) furanone (1.34 g, 0.004M), methanol (25 mL) and piperidine (6 drops) was heated and stirred at reflux for 2.0 hours and then allowed to cool. The orange solid was collected by filtration, washed with methanol and dried in air (yield—0.64 g). Mass spectrometry indicated the desired product XVI, with some half-reacted product XVII also present.

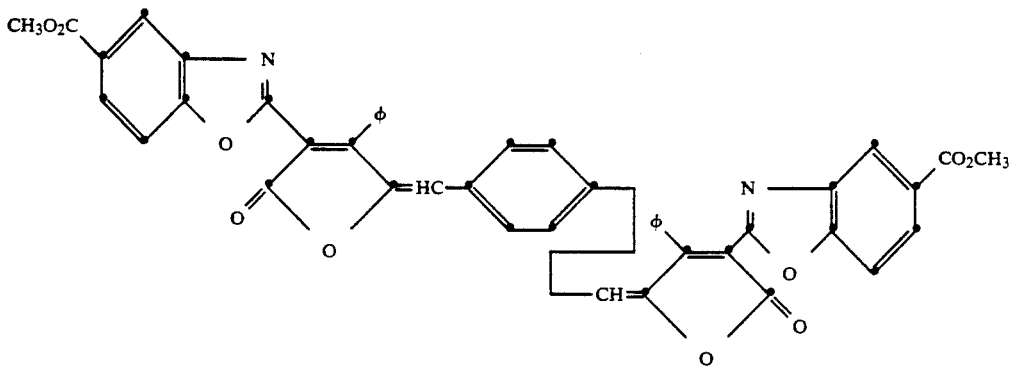

XVI

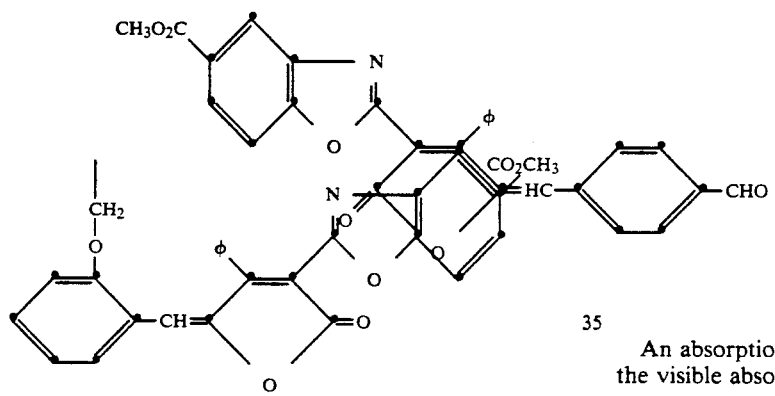

XVII

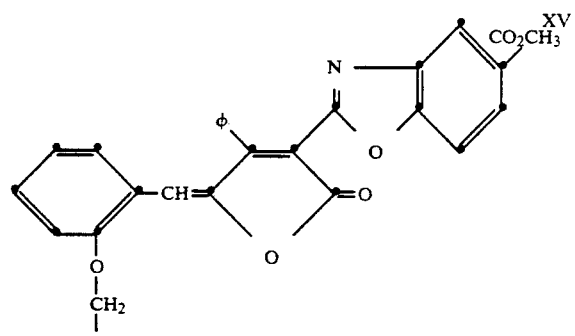

XV

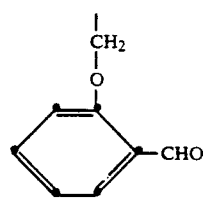

In the UV/vis absorption spectrum in methylene chloride an absorption maximum was observed at 411 nm.

Example 40

A reaction mixture of terephthaldehyde (0.27 g, 0.002M), 3-(5-carbomethoxybenzoxazol-2-yl)-4-phenyl- An absorption maximum was observed at 464 nm in the visible absorption spectrum in methylene chloride.

Examples 41–44 and Comparative Example 1

Dyeings on 100% textured polyester fabric (Dacron) (5.0 g) using the colorants of Examples 12, 13, 14, 16 above and Example III of U.S. Pat. No. 3,661,899, respectively, were performed according to the following procedure: A sample of each colorant (33.4 mg) was dissolved in 10 mL of 2-ethoxyethanol by warming and stirring in a metal dyepot. A solution containing Igepon T-51 (0.1 g) and sodium lignin sulfonate dispersant (0.1 g) in water was added with stirring. To each dyebath were added 0.5% owf (based on the weight of the fabric) Versene 100 and 4.0% owf Hydron JBC carrier. The pH was adjusted to about 5.0 by the addition of acetic acid and water added to give a 30/1 bath ratio. The thoroughly wet fabric was then entered and stirred and all finally transferred into a pressure dyeing container, which was sealed and heated at 265° F. for 1.0 hour. The containers were cooled and the fabric was scoured for 20 minutes at room temperature, using an aqueous solution of 1 g/L neutral soap and 1 g/L sodium carbonate, and then dried by heating at 250° F. for 5 minutes.

The samples were tested for color fastness to dry heat [see AATCC Test Method 117-1984 (AATCC 1986 Technical Manual)] as follows: A 2"×2" square of each dyed fabric was "sandwiched" between a sample of the original undyed fabric and a multifiber test fabric No. 10A (Testfabrics, Inc.) and heated at 350° F. for 1 minute in a Scorch Tester (Atlas Electric Devices) and then removed. Observation of the samples showed that the multifiber and original fabric in contact with the colorant of Example III of U.S. Pat. No. 3,661,899 were heavily stained a red color, while the colorants of Examples 12, 13, 14 and 16 above showed no staining.

Examples 45-48 and Comparative Example 2

Dyeings on 100% textured polyester fabric (Dacron) (5.0 g) were done using the colorants of Examples 12, 13, 14, 16 and Example III of U.S. Pat. No. 3,661,899, respectively, according to the procedure of Examples 41-44 above except that amount of each dye used was 8.4 mg. To determine the effect of higher pH values on the stability of the dyes, the dyeings were repeated adjusting the initial pH readings of the dyebaths at pH6, pH7 and finally pH8 using appropriate quantities of dilute solutions of monosodium phosphate, sodium hydroxide and acetic acid if needed. Observation of the completed dyeings showed that the colorant of Example III of U.S. Pat. No. 3,661,899 had lost much color at pH7, for example, while the colorants of Examples 12, 13, 14 and 16 showed no loss in color at pH7, thus establishing the improved and unexpected improvement in pH stability of the colorants of this application.

Example 49

The following materials were placed in a 500 mL three necked, round bottom flask:

| | |
|---|---|
| 116.18 g (0.599 M) | dimethyl terephthalate |
| 81.0 g (0.90 M) | 1,4-butanediol |
| 0.0133 g | Ti from a n-butanol solution of titanium tetraisopropoxide |
| 1.34 g (.00242 M) | colorant of Example 16 |

The flask was equipped with a nitrogen inlet, stirrer, vacuum outlet, and condensing flask. The flask and contents were heated in a Belmont metal bath with a nitrogen sweep over the reaction mixture as the temperature was increased to 200° C. and then to 230° C. over 2 hours. The temperature was held at 230° C. for 1.0 hour and a vacuum was applied until the pressure was reduced to 0.5 mm Hg. The polycondensation was completed by heating the flask and contents at about 230° C. for 45 minutes under a pressure of 0.1 to 0.5 mm Hg. The vacuum was then relieved with nitrogen and methyl benzoate (125 mL) was added slowly and stirred to solution over about 10 minutes with the flask still in the metal bath. The resulting solution was transferred to a 2 L beaker and stirred until crystallization occurred. Acetone (700 mL) was added slowly with stirring to dilute the slurry and keep it stirrable. The diluted slurry was stirred for 30 minutes, filtered and the cake was washed with acetone. The cake was twice reslurried in acetone and then dried in air. The resulting red semicrystalline polyester powder (122.3 g), containing 1.0 weight percent of the methine colorant residue, had an inherent viscosity of 0.307, a melting temperature of 222° C., a weight average molecular weight owf 17,356, a number average molecular weight of 12,385 and a polydispersity value of 1.40.

Example 50

The following materials were placed in a 500 mL three necked, round bottom flask:

| | |
|---|---|
| 106.27 g (0.548 M) | dimethyl terephthalate |
| 75.60 g (0.84 M) | 1,4-butanediol |
| 0.0134 g | Ti from a n-butanol solution of titanium tetraosopropoxide |
| 13.50 g (0.0244 M) | colorant of Example 16 |

The flask was equipped with a nitrogen inlet, stirrer, vacuum outlet, and condensing flask. The flask and contents were heated in a Belmont metal bath with a nitrogen sweep over the reaction mixture as the temperature was increased to 200° C. and then to 230° C. over 2 hours. A vacuum was applied until the pressure was reduced to 0.5 mm Hg. The polycondensation was completed by heating the flask and contents at about 230° C. for 1.0 hour under a pressure of 0.1 to 0.5 mm Hg. The vacuum was then relieved with nitrogen and methyl benzoate (125 mL) was added slowly and stirred to solution over about 10 minutes with the flask still in the metal bath. The resulting solution was transferred to a 2 L beaker and stirred until crystallization occurred. Acetone (700 mL) was added slowly with stirring to dilute the slurry and keep it stirrable. The diluted slurry was stirred for 30 minutes, filtered and the cake was washed with acetone. The cake was twice reslurried in acetone and then dried in air. The resulting dark red semicrystalline polyester power (118.9 g), containing 10.0 weight percent of the methine colorant residue, had an inherent viscosity of 0.190, a melting temperature of 205° C., a weight average molecular weight of 10,745, a number average molecular weight of 8,039 and a polydispersity value of 1.34.

Example 51

The following materials were placed in a 500 mL three necked, round bottom flask:

| | |
|---|---|
| 111.44 g (0.574 M) | dimethyl terephthalate |
| 81.00 g (0.90 M) | 1,4-butanediol |
| 0.141 g | Ti from a n-butanol solution of titanium tetraisopropoxide |
| 14.40 g (0.0254 M) | colorant of Example 15 |

The flask was equipped with a nitrogen inlet, stirrer, vacuum outlet, and condensing flask. The flask and contents were heated in a Belmont metal bath with a nitrogen sweep over the reaction mixture as the temperature was increased to 200° C. and then to 230° C. over 2 hours. A vacuum was applied until the pressure was reduced to 0.5 mm Hg. The polycondensation was completed by heating the flask and contents at about 230° C. for 1.0 hour under a pressure of 0.1 to 0.5 mm Hg. The vacuum was then relieved with nitrogen and methyl benzoate (125 mL) was added slowly and stirred to solution over about 10 minutes with the flask still in the metal bath. The resulting solution was transferred to a 2 L beaker and stirred until crystallization occurred. Acetone (700 mL) was added slowly with stirring to dilute the slurry and keep it stirrable. The diluted slurry was stirred for 30 minutes, filtered and the cake was washed with acetone. The cake was twice reslurried in acetone and then dried in air. The resulting dark red semicrystalline polyester powder (121.7 g), containing 10.18 weight percent of the methine colorant residue, had an inherent viscosity of 0.151, a melting temperature of 204° C., a weight average molecular weight of 8,424, a number average molecular weight of 6,292 and a polydispersity value of 1.34.

Example 52

The following materials were placed in a 500 mL three necked, round bottom flask:

| | |
|---|---|
| 97 g (0.5 mol) | dimethyl terephthalate |
| 62 g (1.0 mol) | ethylene glycol |
| 0.00192 g | Ti from a n-butanol solution of acetyl triisopropyl titanate |
| 0.0053 g | Mn from an ethylene glycol solution of manganese acetate |
| 0.0345 g | antimony trioxide |
| 0.0072 g | Co from an ethylene glycol solution of cobaltous acetate |
| 0.0192 g (200 ppm) | colorant of Example 16 |

The flask was equipped with a nitrogen inlet, stirrer, vacuum outlet, and condensing flask. The flask and contents were heated at 200° C. in a Belmont metal bath for 60 minutes and at 210° C. for 75 minutes with a nitrogen sweep over the reaction mixture. Then, 1.57 mL of an ethylene glycol slurry of a mixed phosphorous ester composition (Zonyl A) which contained 0.012 g phosphorous was added. The temperature of the bath was increased to 230° C. and a vacuum with a slow stream of nitrogen bleeding in the system was applied over a five minute period until the pressure had been reduced to about 200 mm Hg. The flask and contents were heated at about 230° C. under a pressure of about 200 mm Hg for 25 minutes. The metal bath temperature was then increased to about 270° C. At 270° C., the pressure was slowly reduced to about 100 mm Hg and the flask and contents heated at about 270° C. for 30 minutes. The metal bath temperature was increased to 285° C. and the pressure was reduced slowly to 4.5 mm Hg. The flask and contents were heated at 285° C. under pressure of 4.5 mm Hg for 25 minutes. Then the pressure was reduced to 0.25 mm Hg and polycondensation was continued for 40 minutes. The flask was removed from the metal bath and was allowed to cool in a nitrogen atmosphere while the polymer crystallized. The resulting polymer had an inherent viscosity of 0.52 as measured in a 60/40 ratio by weight of phenol/tetrachloroethane at a concentration of 0.5 g per 100 mL. No loss of colorant by vaporization was observed in the distillate and showed the colorant to have a low degree of volatility.

Examples 53–75

The colorants of Examples 12, 14, 15, 17, 19, 20, 21, 22, 23, 24, 25, 26, 27, 28, 29, 30, 32, 33, 34, 35, 36 and 37 were added to a polyester composition at 200 ppm exactly as described in Example 52, respectively. Essentially no colorant was observed in the distillates during the early stages of the preparations, thus establishing that the colorants have a low degree of volatility.

Comparative Example 3

The colorant of Example III of U.S. Pat. No. 3,661,899 was added to a polyester composition at 200 ppm exactly as described in Example 52. Observation of the distillate showed significant loss of the colorant, thus establishing that the colorant has a high degree of volatility.

TABLE 1

COMPARISON OF ADSORPTION MAXIMA AND EXTINCTION COEFFICIENTS

| Colorant | $\lambda_{max}$, nm ($CH_2Cl_2$) | Extinction Coefficient (E) |
|---|---|---|
| 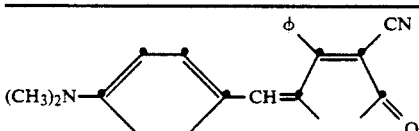<br>Example III of U.S. Pat. No. 3,661,899 | 527 | 52,842 |
| 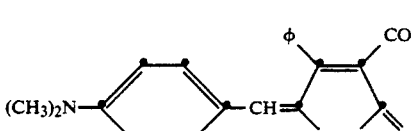<br>Example 22 of U.S. Pat. No. 4,617,373 | 497 | 45,906 |
| 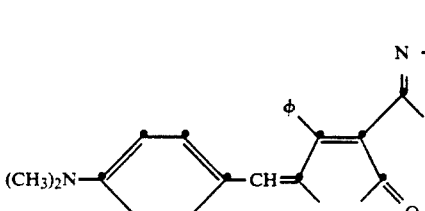<br>Example 13 above | 524 | 49,033 |

TABLE 2

5-ARYLIDENE-3-(CARBOMETHOXYBENZOXAZOL-2-YL-4-PHENYL-2(5H) FURANONES

| Ex. No. | Starting Aldehyde (Ar—CHO) | Ar— | λmax, nm (solvent) | Extinction Coefficient (E) |
|---|---|---|---|---|
| 26 | N-Methylpyrrole-2-carboxaldehyde | N-methylpyrrol-2-yl | 480 (CH$_2$Cl$_2$) | 41,807 |
| 27 | 1,4-Benzodioxan-6-carboxaldehyde | 1,4-benzodioxan-6-yl | 428 (CH$_2$Cl$_2$) | 27,437 |
| 28 | N-Ethyl-3-carbazole-carbonaldehyde | N-ethylcarbazol-3-yl | 478 (CH$_2$Cl$_2$) | 27,772 |
| 29 | 4-(Methylthio)benzaldehyde | 4-(CH$_3$S)C$_6$H$_4$— | 436 (CH$_2$Cl$_2$) | 32,578 |
| 30 | Methyl 4-formylbenzoate | 4-(CH$_3$O$_2$C)C$_6$H$_4$— | 383 (CH$_2$Cl$_2$) | 35,128 |
| 31 | 2-Dimethylaminobenzaldehyde | 2-(N(CH$_3$)$_2$)C$_6$H$_4$— | {370 {443 (CH$_2$Cl$_2$) | 23,925} 18,994} |
| 32 | 1,3-Diphenyl-4-pyrazole carboxaldehyde | 1,3-diphenylpyrazol-4-yl | 432 (CH$_2$Cl$_2$) | 36,212 |
| 33 | 3-Methoxysalicylaldehyde (o-vanillin) | 3-CH$_3$O-2-HO-C$_6$H$_3$— | 407 (CH$_2$Cl$_2$) | 30,578 |

TABLE 2-continued

5-ARYLIDENE-3-(CARBOMETHOXYBENZOXAZOL-2-YL-4-PHENYL-2(5H) FURANONES

| Ex. No. | Starting Aldehyde (Ar—CHO) | Ar— | λmax, nm (solvent) | Extinction Coefficient (E) |
|---|---|---|---|---|
| 34 | 3-Hydroxy-4-methoxy-benzaldehyde (iso-vanillin) | (4-hydroxy-3-methoxyphenyl) | 441 (CH$_2$Cl$_2$) | 34,250 |
| 35 | 2,5-Dimethyl-1-phenyl-3-pyrrole carboxaldehyde | (2,5-dimethyl-1-phenyl-pyrrol-3-yl) | 477 (CH$_2$Cl$_2$) | 45,024 |
| 36 | 3-(4-Dimethylamino)-phenyl-1,2,2-trimethyl-5-indolecarboxaldehyde | (3-(4-dimethylaminophenyl)-1,2,2-trimethyl-indol-5-yl) | {347 {548 (CH$_2$Cl$_2$) | 26,849} 29,198} |
| 37 | N-Phenylphenothiazine-4-carbonaldehyde | (N-phenylphenothiazin-4-yl) | {377 {532 (CH$_2$Cl$_2$) | 24,751} 29,019} |

TABLE 3

| Ex. No. | R₁₉ | X | Z₂ | R₁ | R₂ | R₃ |
|---|---|---|---|---|---|---|
| 76 | 5-CO₂C₄H₉-n | C₆H₅ | S | H | C₂H₅ | C₂H₄OH |
| 77 | 6-NHCOC₆H₁₁ | C₆H₄-3,4-diOCH₃ | S | H | C₂H₄OH | C₂H₄OH |
| 78 | 6-NHCOCH₂OH | C₆H₄-3,4-diCH₃ | S | H | C₂H₅ | CH₂CH₂CO₂C₂H₅ |
| 79 | 6-NHCOC₆H₅ | C₆H₄-4-CO₂CH₃ | S | H | C₆H₁₁ | CH₂CH₂OH |
| 80 | 6-NHCOCH₃ | C₆H₅ | S | H | CH₃ | CH₂C₆H₄-p-CO₂CH₃ |
| 81 | CH₂—5-SO₂NC₂H₄OH | C₆H₅ | O | 3-CH₃OH | CH₂CH₃ | CH₂CH₃ |
| 82 | 5-SO₂NHCH₂C(CH₃)₂CH₂OH | C₆H₅ | O | 3-CH₂CH₂OCOCH₃ | CH₃ | CH₃ |
| 83 | 5,6-di-Cl | C₆H₅ | S | 3-CH₃ | CH₂CH₂OCOC₂H₅ | CH₂CH₂OCOC₂H₅ |
| 84 | 6-CN | C₆H₄-4-OC₂H₄OH | S | 3-Cl | C₂H₅ | CH₂CH₂COOH |
| 85 | 5-CO₂CH₃ | C₆H₅ | O | 3-Br | CH₂CH₂CH₃ | CH₂CH₂OCH₂CH₂OCOCH₃ |
| 86 | 5-CO₂C₂H₅ | C₆H₄-4-OCH₃ | O | H | CH₂CH(CH₃)₂ | CH₂CH₂SCH₂CH₂OH |
| 87 | 5-COOH | C₆H₄-2-OC₂H₅ | O | H | C₂H₅ | C₂H₄OH |
| 88 | 5-CO₂C₂H₄OH | C₆H₄-4-OC₂H₅ | O | H | C₆H₅ | CH₂CH₂OCOCH₃ |
| 89 | 5-SO₂NHC₂H₄OH | C₆H₅ | O | H | CH(CH₃)₂ | (CH₂)₄OH |
| 90 | 5-SO₂C₂H₄OH | C₆H₃-3,4-di-Cl | O | H | C₇H₁₃ | CH₂CH(CH₃)OH |
| 91 | 5-N(SO₂CH₃)C₂H₄OH | C₆H₅ | O | H | C₄H₉-n | CH₂CH₂SO₂C₂H₄OH |
| 92 | 5-SO₂NHC₂H₄OH | C₆H₄-4-SCH₃ | O | H | CH₂CH₂OCOCH₃ | CH₂CH₂OCOCH₂CN |
| 93 | 6-OCH₃ | C₆H₅ | S | 3-OCH₃ | | CH₂CH₂OCOCH₃ |

TABLE 3-continued

| Ex. No. | R₁₉ | X | Z₂ | R₁ | R₂ | R₃ |
|---|---|---|---|---|---|---|
| 94 | 4-CH₃ | C₆H₄-4-Br | S | 3-OC₂H₅ | CH₂CH₂OCO₂C₂H₅ | CH₂CH₂OCO₂C₂H₅ |
| 95 | 5-CO₂C₂H₄OC₂H₅ | C₆H₅ | O | 3-CH₃ | CH₂CH₂OCOCH₃ | CH₂CH₂OCOCH₂OCOCH₃ |
| 96 | 5-CO₂C₂H₄OH | C₆H₄-4-NHCOCH₃ | O | 3-C₂H₅ | CH₂CH₃ | CH₂CH(OH)CH₂OH |
| 97 | 5-CO₂CH₂CH₂CN | C₆H₄-4-NHSO₂C₆H₅ | O | 3-Cl | CH₂CH₃ | CH₂CH(OCOCH₃)CH₂OCOCH₃ |
| 98 | 5-COOH | C₆H₄-4-NHSO₂CH₃ | O | 3-Br | CH₂CH₂OCH₂CH₂OCOCH₃ | CH₂CH₂OCH₂CH₂OCOCH₃ |
| 99 | 5-SO₂N(C₂H₄OH)₂ | C₆H₅ | S | H | CH₃ | CH₃ |
| 100 | 5-SO₂N(C₃H₆OH)₂ | C₆H₅ | S | H |  | —CH₂CH₂SO₂CH₂CH₂— |
| 101 | 5:SO₂CH₂CH₂CH(OH)CH₂OH | C₆H₅ | S | H |  | —CH₂CH₂SCH₂CH₂— |
| 102 | 5-SCH₂CH₂OH | C₆H₅ | S | H |  | —CH₂CH₂CH₂CH₂— |
| 103 | 5-SCH₂C₆H₄-4-CO₂H | C₆H₄-4-OC₂H₅ | O | 3-CH₃ |  | —CH₂CH₂N(COCH₃)CH₂CH₂— |
| 104 | 5-SO₂CH₂C₆H₅ | C₆H₅ | O | 3-OCH₃ |  | —CH₂CH₂CH₂CH₂— |
| 105 | 5-SO₂CH₂CH₃ | C₆H₅ | O | H |  | —CH₂CH₂OCOCH₂— |
| 106 | 5-SO₂C₄H₉-n | C₆H₅ | O | 3-OC₂H₄OH | C₆H₅ | CH₂CH₂OH |
| 107 | 5,6-diCl | C₆H₅ | O | 2-OCH₃,5-CH₃ | C₂H₅ | CH₂CH₂OCOCH₃ |
| 108 | H | C₆H₅ | S | 2,5-di-OCH₃ | CH₂CH₂OCOC₆H₁₁ | CH₂CH₂OCOC₆H₁₁ |
| 109 | H | C₆H₅ | S | 2,5-di-OC₂H₅ | CH₂CH₂OH | CH₂CH₂OH |
| 110 | 5-SO₂N(CH₃)₂ | C₆H₅ | S | H | C₂H₅ | CH₂CH₂OC₆H₄-p-COOH |
| 111 | 5-SO₂NHC₆H₁₁ | C₆H₅ | S | H | C₂H₅ | CH₂CH₂OC₆H₄-m-CO₂CH₃ |
| 112 | 5-SO₂NHC₆H₅ | C₆H₅ | S | H | C₂H₅ | CH₂CH₂SC₆H₄-o-COOH |
| 113 | 5-CONHC₂H₄OH | C₆H₅ | S | H | C₂H₅ | ![3-SO₂NHCH₂CO₂C₂H₅-benzyl] |
| 114 | 5-CONH₂ | C₆H₅ | O | H | C₂H₅ | ![3-SO₂N(C₂H₄OH)₂-benzyl] |
| 115 | 6-CON(C₂H₅)₂ | C₆H₅ | O | H | C₂H₅ | ![4-SO₂N(C₂H₄OH)₂-phenoxyethyl CH₂CH₂O-C₆H₄-SO₂N(C₂H₄OH)₂] |
| 116 | 6-CO₂C₂H₅ | C₆H₅ | O | H | C₂H₅ | —CH₂CH₂NHCH₂CH₂— |
| 117 | 6-SO₂C₆H₅ | C₆H₅ | O | H | C₂H₅ | CH(CH₃)CH₂CO₂C₂H₅ |
| 118 | 6-SO₂NHC₆H₁₁ | C₆H₅ | O | H | C₂H₅ | C₂H₅ |
| 119 | 6-CO₂C₆H₁₁ | C₆H₅ | S | H | CH₂CH₂OH | CH₂CH₂COOH |
| 120 | 6-CO₂CH₂C₆H₅ | C₆H₅ | S | H | C₂H₅ | C₆H₅ |
| 121 | 5-CH₂CO₂H | C₆H₅ | O | H | C₂H₅ | CH₂CH₂OC(=O)NHC₂H₅ |

TABLE 3-continued

| Ex. No. | R₁₉ | X | Z₂ | R₁ | R₂ | R₃ |
|---|---|---|---|---|---|---|
| 122 | 5-OCH₂CO₂H | C₆H₅ | O | H | C₂H₅ | CH₂CH₂OCNHC₆H₅ (C=O) |
| 123 | 5,6-di-Cl | C₆H₅ | S | H | C₂H₅ | CH₂CH₂OCN(C₂H₅)₂ (C=O) |
| 124 | 5-SO₂NHCH₂CO₂C₂H₅ | C₆H₅ | O | H | C₂H₅ | CH₂CH₂OCO₂C₂H₅ |
| 125 | 5-SO₂NH₂ | C₆H₅ | O | H | C₂H₄OCOCH₃ | C₂H₄O₂COCH₃ |
| 126 | 5-SO₂NH—C₆H₄—CH₂OH (para) | 5-SO₂NH—C₆H₄—CH₂OH (meta) / C₆H₅ | O | H | C₂H₄OCOH | C₂H₄O₂COH |

TABLE 4

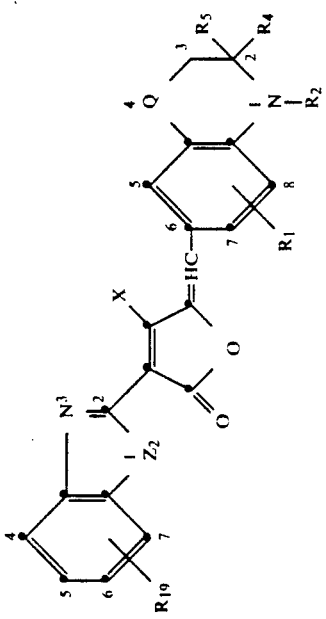

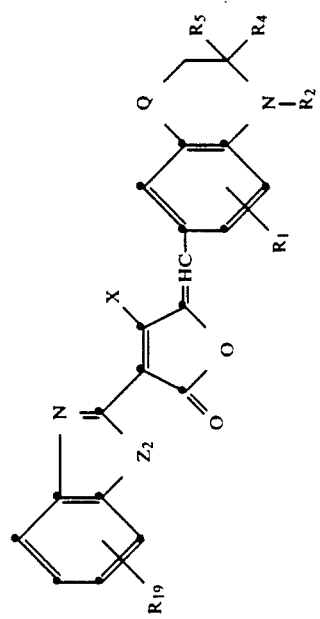

| Ex. No. | R19 | X | Z2 | R1 | R2 | R4 | R5 | Q |
|---|---|---|---|---|---|---|---|---|
| 127 | 5-CO2C4H9-n | C6H5 | O | H | CH2CH2OCOCH3 | | | |
| 128 | 5-CO2CH3 | C6H5 | O | H | CH2CH2OCO2C2H5 | | | |
| 129 | 5-SO2N(CH3)C2H4OH | C6H5 | S | H | CH2CH2OH | | | |
| 130 | 6-SO2CH3 | C6H4-4-CH3 | O | H | CH2C6H4-p-CO2CH3 | | | |
| 131 | 5-SO2CH3 | C6H4-4-Br | S | H | CH2CH(CH3)OH | | | |
| 132 | 5,6-di-Cl | C6H4-4-Cl | O | H | CH2CH2OCH2CH2OH | H | H | —CH2— |
| 133 | 5-NHCOC2H5 | C6H5 | S | 7-CH3 | CH2CH2OH | CH3 | H | —CH2— |
| 134 | 5-CO2C2H4Cl | C6H5 | O | 7-OC2H5 | CH2C6H4-p-CO2CH3 | CH3 | H | —CH2— |
| 135 | 5-CO2C2H4OH | C6H5 | O | 7-Cl | CH2CH2OH | H | CH3 | —CH2— |
| 136 | H | C6H5 | O | 7-OC2H5 | CH2CH2OCOCH3 | CH3 | CH3 | —CH(CH3)— |
| | | | | | | CH3 | CH3 | —CH(CH3)— |
| | | | | | | CH3 | H | —CH(CH3)— |
| | | | | | | CH3 | | —CH2— |
| 137 | H | C6H5 | S | H | CH2CH2OC6H4m-CO2CH3 | CH3 | H | —CH2— |
| 138 | 5-CO2CH3 | C6H5 | O | 7-CH3 | CH2CH2OCOCH3 | CH3 | CH3 | —CH(CH3)— |
| 139 | H | C6H5 | O | 7-CH2OCOCH3 | CH2CH(CH3)OH | CH3 | CH3 | —CH(CH3)— |
| 140 | H | C6H4-2-OCH3 | S | 7-CH2OH | C2H5 | CH3 | CH3 | —CH(CH3)— |
| 141 | H | C6H5 | O | H | CH2CH(OCO2C2H5)CH2OCO2C2H5 | CH3 | CH3 | —CH(CH3)— |
| 142 | 5-CO2CH3 | C6H5 | O | H | CH2C6H4-p-CO2CH3 | CH3 | CH3 | —CH(CH3)— |
| 143 | 5-CO2CH3 | C6H5 | O | H | CH2CH2OC6H4-m-CO2CH3 | CH3 | CH3 | —CH(CH3)— |

TABLE 4-continued

| Ex. No. | R19 | X | Z2 | R1 | R2 | R4 | R5 | Q |
|---|---|---|---|---|---|---|---|---|
| 144 | H | C6H5 | O | H | 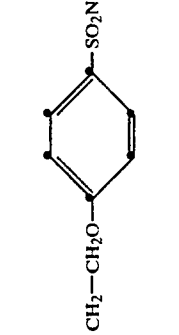 | H | H | —CH2— |
| 145 | 5-CH3 | C6H5 | O | H | 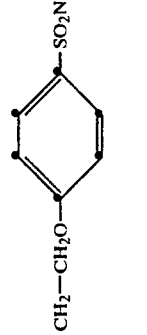 | H | H | —CH2— |
| 146 | 6-CH3 | C6H4-4-OC2H4OH | S | H | CH2C6H11 | H | H | —CH2— |
| 147 | 5-CO2C2H4OH | C6H5 | O | H | CH2CH2OCOCH2OH | H | H | —CH2— |
| 148 | H | C6H5 | O | H | CH2CH2OCONHC6H5 | H | H | —CH2— |
| 149 | 5-CO2CH3 | C6H5 | O | H | CH2CH2OCONH2 | H | H | —CH2— |
| 150 | 5-CO2CH3 | C6H5 | S | H | CH2CH2OH | H | H | —CH2— |
| 151 | 5-CO2CH3 | C6H5 | S | 5-CH3-8-OCH3 | C2H5 | H | H | —CH(CH3)— |
| 152 | 5-CO2CH3 | C6H5 | S | 8-OCH3 | CH2CH2OH | CH3 | CH3 | —CH(CH3)— |
| 153 | 5-CO2CH3 | C6H5 | O | H | CH2CH2OCOCH3 | CH3 | CH3 | —CH2— |
| 154 | 5-CO2CH3 | C6H5 | O | H | CH2CH2OC6H4-p-CO2CH3 | CH3 | H | —CH2— |
| 155 | 5-CO2CH3 | C6H5 | O | H | CH2CH2OCOCH3 | H | H | —CH2— |
| 156 | 5-CO2CH3 | C6H5 | S | H | CH2C6H4-p-CO2CH3 | H | H | —CH2— |
| 157 | 5-CO2CH3 | C6H5 | O | 7-CH3 | CH2CH2OH | CH3 | H | —O— |
| 158 | 5-CO2C2H4OH | C6H5 | O | H | CH2CH(OCOCH3)CH2OCOCH3 | CH3 | H | —O— |
| 159 | 6-SO2C2H5 | C6H5 | S | H | CH2CH2OCH2CH2OH | CH3 | H | —O— |
| 160 | H | C6H5 | O | 7- | CH3 | CH | H | —O— |
| 161 | H | C6H5 | S | H | C4H9-n | CH3 | H | —O— |
| 162 | 5-CO2CH3 | C6H5 | O | H | CH2CH2OCO2C2H5 | CH3 | H | —O— |
| 163 | 5-CO2C2H4OCH3 | C6H5 | O | H | CH2C6H5 | CH3 | H | —O— |
| 164 | 5-SO2NHC2H4OH | C6H5 | S | H | C2H5 | CH3 | H | —O— |

TABLE 5

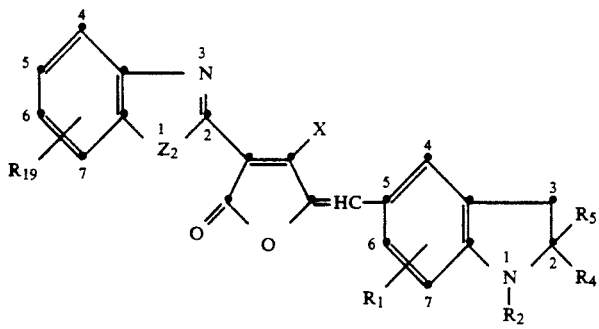

| Ex. No. | $R_{19}$ | X | $Z_2$ | $R_1$ | $R_2$ | $R_4$ | $R_5$ |
|---|---|---|---|---|---|---|---|
| 165 | 5-$CO_2CH_3$ | $C_6H_5$ | O | H | $C_2H_4OCOCH_3$ | H | H |
| 166 | 5-$CO_2CH_3$ | $C_6H_5$ | S | H | $C_2H_4OCOCH_3$ | $CH_3$ | H |
| 167 | H | $C_6H_5$ | O | H | $CH_2C_6H_4$-p-$CO_2CH_3$ | H | H |
| 168 | H | $C_6H_5$ | O | H | $CH_2CH(OCOCH_3)CH_2OCOCH_3$ | H | H |
| 169 | 5-$CO_2C_2H_4OH$ | $C_6H_5$ | O | H | $CH_2CH_2OH$ | $CH_3$ | H |
| 170 | 5-$CO_2CH_3$ | $C_6H_5$ | S | H | $C_2H_5$ | H | H |
| 171 | 5-$CO_2H$ | $C_6H_5$ | O | H | $CH_2CH_2OCH_2CH_2OH$ | H | H |

TABLE 6

Bis-Methine Compounds

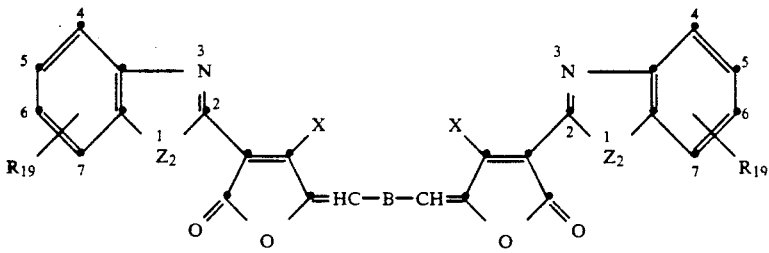

| Ex. No. | B | $R_{19}$ | X | $Z_2$ |
|---|---|---|---|---|
| 172 | ![phenyl-OCH2CH2O-phenyl] | 5-$CO_2CH_3$ | $C_6H_5$ | O |
| 173 | ![phenyl(OCH3)-OCH2CH2O-phenyl(CH3O)] | 5-$CO_2CH_3$ | $C_6H_5$ | S |
| 174 | ![phenyl-N(C2H5)-CH2CH2-N(C2H5)-phenyl] | H | $C_6H_5$ | O |
| 175 | ![phenyl-N(C2H5)-C2H4OC2H4-N(C2H5)-phenyl] | 5-$CO_2CH_3$ | $C_6H_5$ | O |

TABLE 6-continued
Bis-Methine Compounds
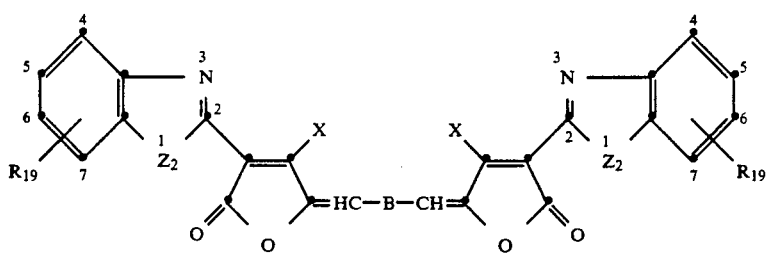
| Ex. No. | B | R$_{19}$ | X | Z$_2$ |
|---|---|---|---|---|
| 176 | 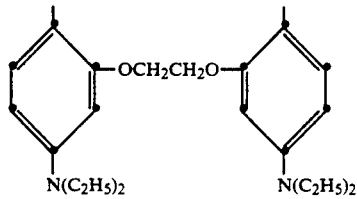 | 5-CO$_2$CH$_3$ | C$_6$H$_5$ | O |
| 177 | 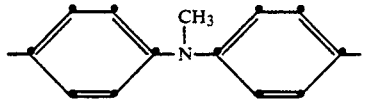 | 5-CO$_2$CH$_3$ | C$_6$H$_5$ | O |
| 178 | 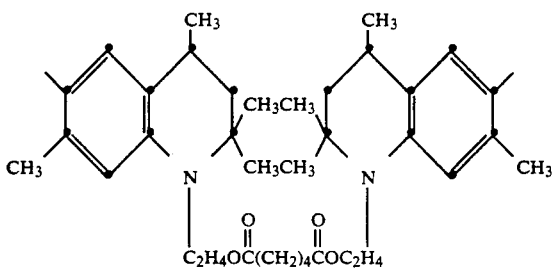 | H | C$_6$H$_5$ | O |
| 179 | 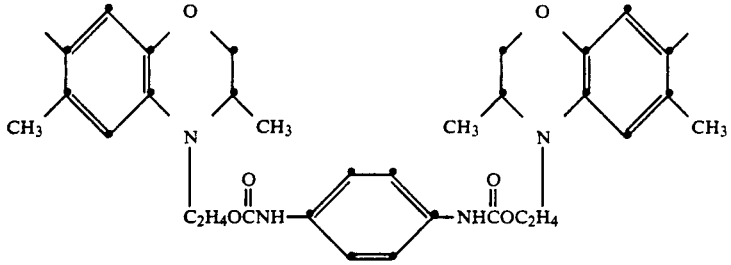 | H | C$_6$H$_5$ | S |
| 180 |  | H | C$_6$H$_5$ | S |
| 181 | 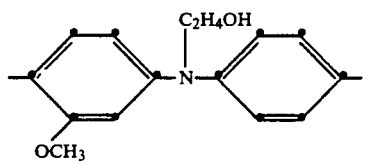 | H | C$_6$H$_5$ | O |
We claim:
1. A polyester composition having copolymerized therein at least 0.001 weight percent of a residue of a light absorbing compound of formulae (II) or (III):

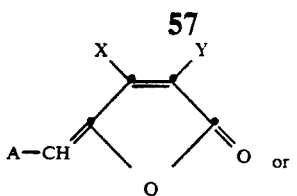

(II)

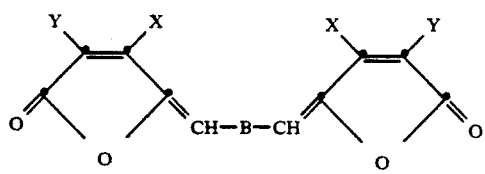

(III)

wherein X is phenyl or phenyl substituted by a group selected from the group consisting of lower alkyl; lower alkoxy; halogen; hydroxy; cyano; —NHCOR$_{17}$; —N(R$_{17}$)SO$_2$R$_{16}$; —SO$_2$R$_{16}$; —CO$_2$R$_{16}$; and lower alkyl substituted with hydroxy, lower alkoxy, halogen or alkanoyloxy, wherein R$_{16}$ and R$_{17}$ are as defined below;

wherein Y is a benzoxazol-2-yl or benzothiazol-2-yl radical, or a group having the following formula

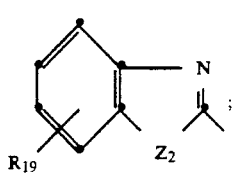

wherein Z$_2$ is —O— or —S—; R$_{19}$ is one or more lower alkyl, lower alkoxy, —O—lower alkylene—CO$_2$R$_{17}$, lower alkylene—CO$_2$R$_{17}$, halo, cyano, —SO$_2$R$_{16}$, —NHCOR$_{17}$, —(R$_{17}$)SO$_2$R$_{16}$, —CO$_2$R$_{17}$, —CON(R$_{17}$)R$_{18}$, or —SO$_2$N(R$_{17}$)R$_{18}$ groups, wherein R$_{18}$ is as defined below;

wherein A is selected from groups of the formulae

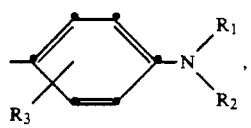

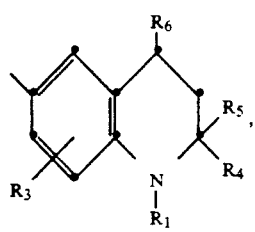

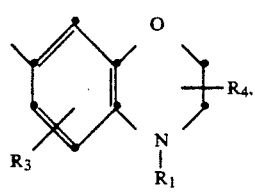

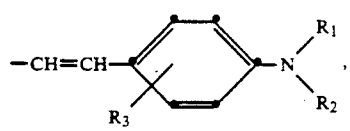

-continued

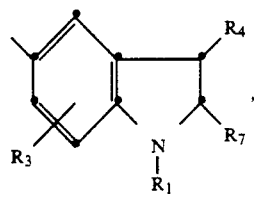

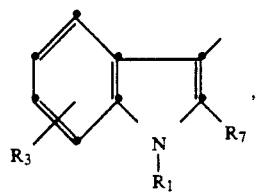

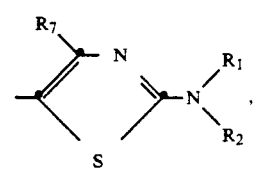

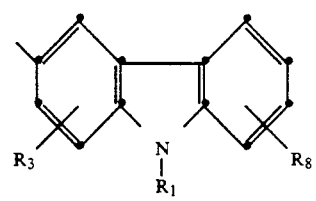

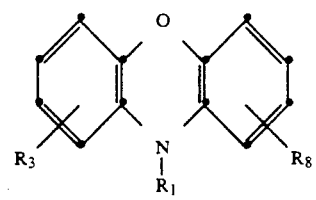

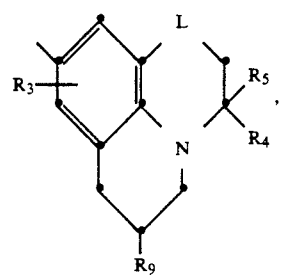

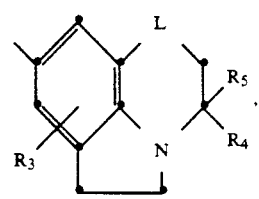

-continued
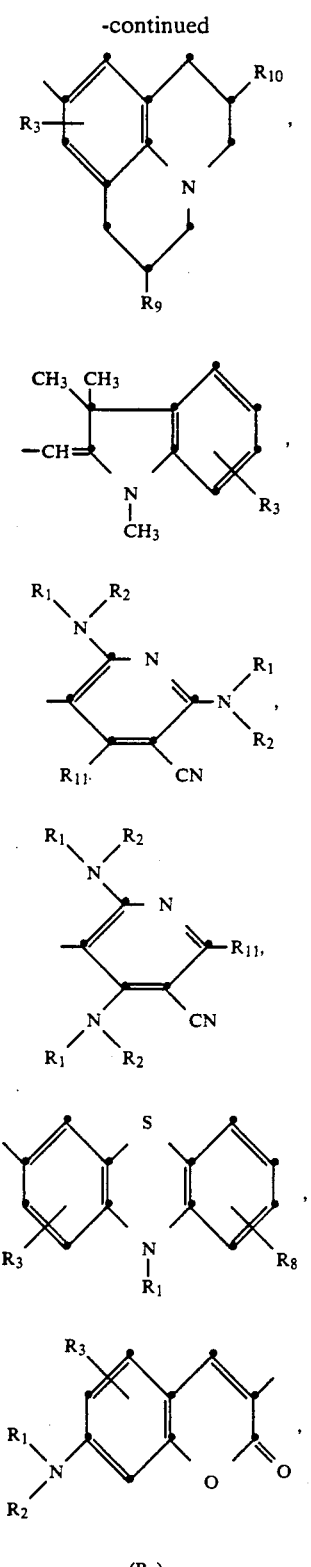
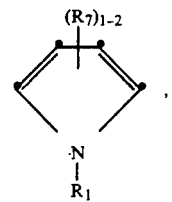
-continued
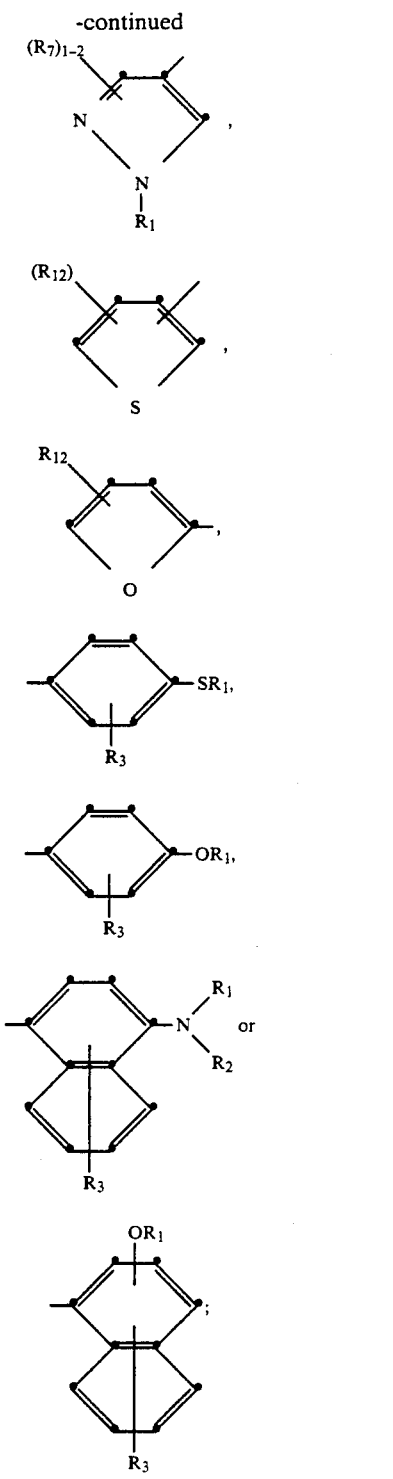
and B is selected from the following formulae:
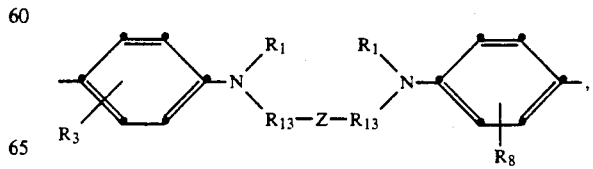

61

-continued

[chemical structure with R1, R3, R8, N]

[chemical structure with R3, R8, O—R13—Z—R13—O]

[chemical structure with R3]

[chemical structure with R3, R8, O—R13—Z—R13—O, N(R1)(R2), N(R1)(R2)]

[chemical structure with R3, R4, R5, R6, N—R13—Z]$_2$ or

[chemical structure with R3, R4, O, N—R13—Z]$_2$;

wherein $R_1$ and $R_2$ are selected from alkyl, alkenyl, alkynyl, cycloalkyl, phenyl, alkyl substituted with one or more of the following groups:

cycloalkyl; cycloalkyl substituted by a group selected from the group consisting of lower alkyl, lower alkoxy, hydroxy, and alkanoyloxy; phenyl; phenyl substituted by a group selected from the group consisting of lower alkyl, lower alkoxy, halogen, hydroxy, cyano, —NHCOR$_{17}$, —N(R$_{17}$)SO$_2$R$_{16}$, SO$_2$R$_{16}$, —CO$_2$R$_{16}$, and lower alkyl substituted with hydroxy, lower alkoxy, halogen or alkanoyloxy; cyano; halogen; 2-pyrrolidino; phthalimidino; vinylsulfonyl; acrylamido; o-benzoic sulfimido; alkoxy; alkoxyalkoxy; cyanoalkoxy; hydroxy; hydroxyalkoxy; phenoxy; phenoxy substituted with lower alkyl, lower alkoxy or halogen; groups of the formulae;

62

[chemical structure] —N(CO-Y'-CO), —X$_1$—CH$_2$CH$_2$N(CO-Y'-CO),

—X$_1$—CH$_2$CH$_2$SR$_{14}$, —S—R$_{14}$,

[chemical structure] —S—C(=N-N(R$_{15}$))CH=N, —X$_1$—CH$_2$CH$_2$—S—C(=N-N(R$_{15}$))CH=N, $$-OCR_{16}, -OCOR_{16}, -CO_2R_{16}, -N(R_{17})SO_2R_{16},$$

$$-OCN(R_{17})R_{18}, -NHCN(R_{17})R_{18}, -CN(R_{17})R_{18},$$

$$-SO_2N(R_{17})R_{18}, SO_2R_{16} \text{ or } -NHCR_{17};$$

wherein $X_1$ is selected form —O—, —S—, or —SO$_2$—; $Y_1$ is selected from $C_2$-$C_3$ alkylene, vinylene, o-phenylene and o-phenylene substituted with lower alkyl, lower alkoxy, halogen, carboxy, alkoxycarbonyl or nitro; —OCH$_2$—; —OCH$_2$CH$_2$—; —CH$_2$OCH$_2$—; —S—CH$_2$—; —CH$_2$SCH$_2$—; —NHCH$_2$—; —NHCH$_2$CH$_2$—; —N(alkyl)CH$_2$—; —N(alkyl)CH$_2$CH$_2$— or NHC(C$_6$H$_5$)$_2$—;

wherein $R_{14}$ is selected form lower alkyl; cycloalkyl; phenyl; phenyl substituted with one or more groups selected from lower alkyl, lower alkoxy or halogen; a heterocyclic ring selected from pyridyl, pyrimidinyl, benzoxazolyl, benzothiazolyl, benzimidazol, 1,3,4-thiadiazolyl, and 1,3,4-oxodiazolyl, said heterocyclic ring optionally substituted with one or more groups selected from lower alkyl, lower alkoxy or halogen;

$R_{15}$ is selected from hydrogen, lower alkyl; alkyl substituted with hydroxy, alkanoyloxy, lower alkoxy, halogen, cyano, carbalkoxy or phenyl;

$R_{16}$ is selected from cycloalkyl; cycloalkyl substituted with lower alkyl; allyl; phenyl; phenyl substituted with one or more groups selected from lower alkyl, lower alkoxy or halogen, lower alkyl; lower alkyl substituted with one or more groups selected from lower alkoxy, halogen, phenyl, cyano, cycloalkyl, phenoxy, lower alkylthio, hydroxy, alkanoyloxy, alkoxycarbonyl or lower alkylsulfonyl;

and $R_{17}$ and $R_{18}$ are each independently selected from hydrogen or those groups represented by $R_{16}$; cycloalkyl substituted with one or more groups selected from the group consisting of lower alkyl, lower alkoxy, hydroxy, an alkanoyloxy; and phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; or $R_1$ or $R_2$ are combined with the nitrogen to which they are attached to form an A radical having the formula

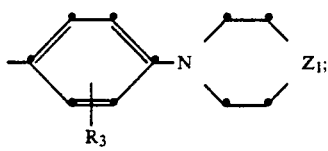

wherein $Z_1$ is selected from a convalent bond, —$CH_2$—, —O—, —S—, —$SO_2$—, —CO—, —$CO_2$—, —NH—, —N($R_1$)—, N(COR$_1$)— or —N($SO_2R_1$)—; $R_3$ and $R_8$ are hydrogen or 1-2 substituents selected from lower alkyl, lower alkoxy or halogen; $R_4$, $R_5$ and $R_6$ are hydrogen or lower alkyl; $R_7$ is hydrogen, lower alkyl, phenyl or phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; $R_9$ and $R_{10}$ are selected from hydrogen, lower alkyl, lower alkoxy, hydroxy, halogen or alkanoyloxy; $R_{11}$ is lower alkyl; phenyl or phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; $R_{12}$ is hydrogen or 1-2 substituents selected from lower alkyl; lower alkoxy; lower alkylthio; alkenyl; cycloalkyl; lower alkyl substituted with lower alkoxy, hydroxy, alkanoyloxy or phenyl; phenyl; phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; or halogen; $R_{13}$ is lower alkylene; lower alkylene substituted by one or more lower alkoxy, halogen, phenyl, hydroxy, or alkanoyloxy groups; alkylene oxyalkylene, phenylene; phenylene substituted by a group selected from the group consisting of lower alkoxy, halo, phenyl, hydroxy, and alkanoyloxy; phenylenealkylene; or cycloalkylene; Z is a direct bond, —OCO$_2$—, —O$_2$C—, —O—, —SO$_2$—, —S—, —S—S—, R$_1$SO$_2$—N=, —O$_2$C— lower alkylene —CO$_2$—, phenylene, —O$_2$C— phenylene—CO$_2$—, —O$_2$C— substituted phenylene—CO$_2$—, wherein phenylene is substituted by a group selected from the group consisting of lower alkoxy, halo, phenyl, hydroxy, and alkanoyloxy, —O$_2$CNH—alkylene—NHCO$_2$—, —O$_2$CNH—phenylene—NHCO$_2$— or —O$_2$CNH—substituted phenylene-NHCO$_2$—, wherein phenylene is substituted by a group selected from the group consisting of lower alkoxy, halo, phenyl, hydroxy, and alkanoyloxy; L is selected from a direct bond, —O—, —CH$_2$—or —CH(CH$_3$)—.

2. The polyester composition of claim 1, wherein A is selected from groups of the formula

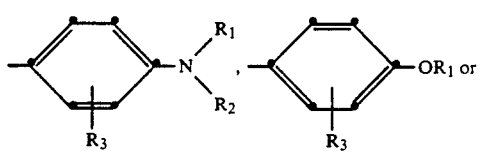

-continued

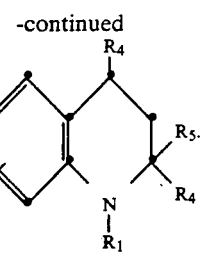

3. The polyester composition of claim 1, wherein X is phenyl and Y is a 5-alkoxycarbonylbenzoxazol-2-yl radical.

4. The polyester composition of claim 1, wherein X is phenyl and Y is a 5-alkoxycarbonylbenzothiazol-2-yl radical.

5. An amorphous light absorbing concentrate comprising an amorphous polyester having copolymerized therein at least about 5.0 weight percent of a residue of a light absorbing compound of formulae (II) or (III):

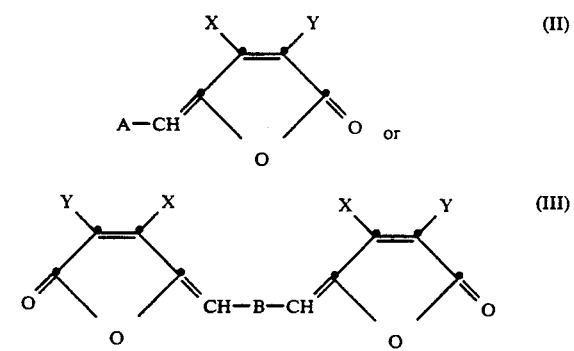

wherein X is phenyl or phenyl substituted by a group selected from the group consisting of lower alkyl; lower alkoxy; halogen, hydroxy; cyano; —NHCOR$_{17}$; —N(R$_{17}$)SO$_2$R$_{16}$; —SO$_2$R$_{16}$; —CO$_2$R$_{16}$; and lower alkyl substituted with hydroxy, lower alkoxy, halogen or alkanoyloxy, wherein R$_{16}$ and R$_{17}$ are as defined below;

wherein Y is a benzoxazol-2-yl or benzothiazol-2-yl radical, or a group having the following formula

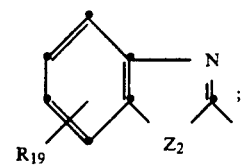

wherein $Z_2$ is —O— or —S—; $R_{19}$ is one or more lower alkyl, lower alkoxy, —O—lower alkylene—CO$_2$R$_{17}$, lower alkylene—CO$_2$R$_{17}$, halo, cyano, —SO$_2$R$_{16}$, —NHCOR$_{17}$, —(R$_{17}$)SO$_2$R$_{16}$, —CO$_2$R$_{17}$, —CON(R$_{17}$)R$_{18}$, or —SO$_2$N(R$_{17}$)R$_{18}$ groups, wherein R$_{18}$ is as defined below;

wherein A is selected from groups of the formulae

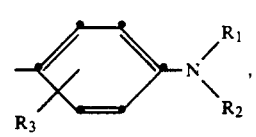

-continued
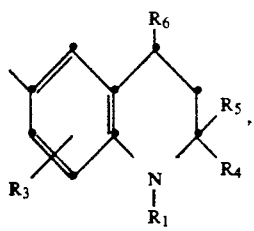
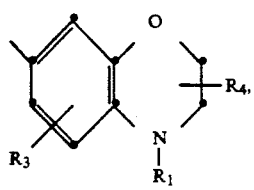
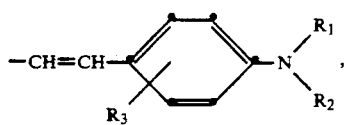
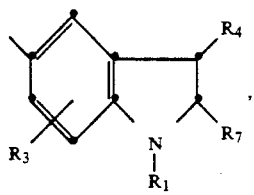
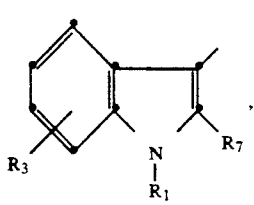
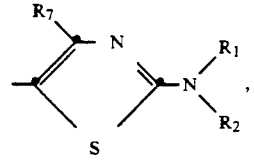
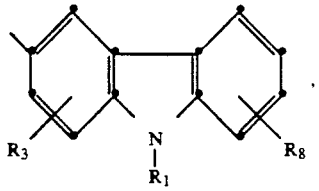
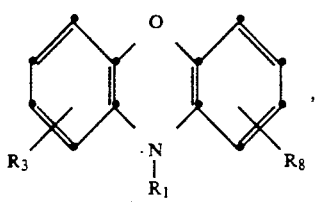
-continued
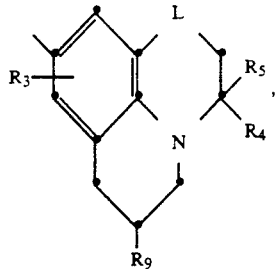
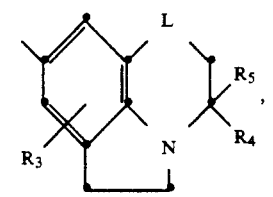
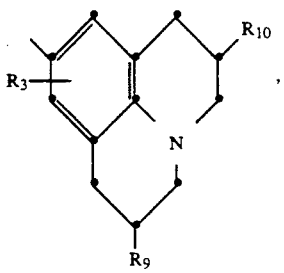
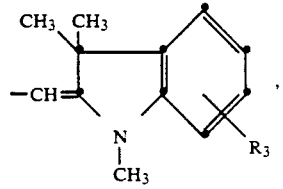
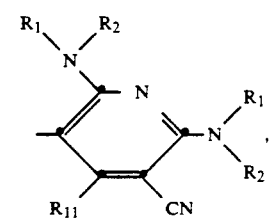
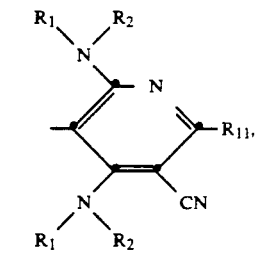
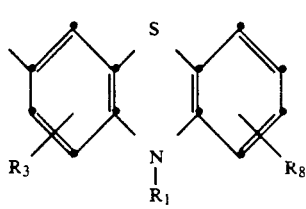

-continued
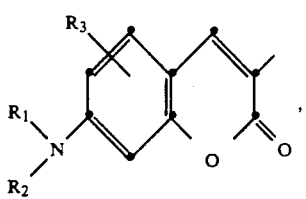
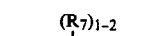
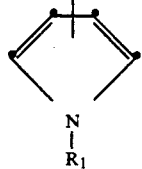
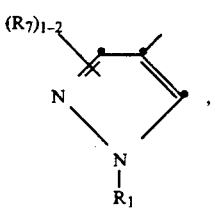
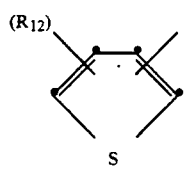
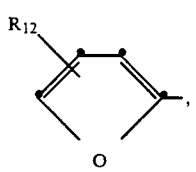
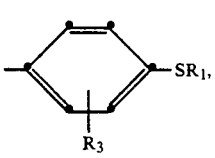
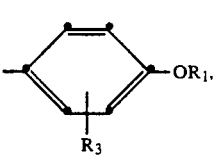
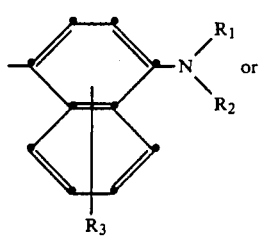
-continued
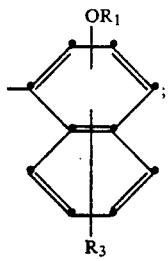
and B is selected from the following formulae:
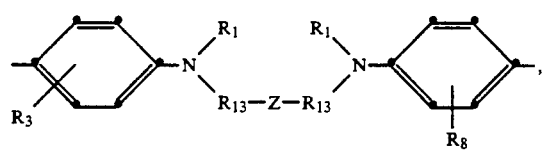
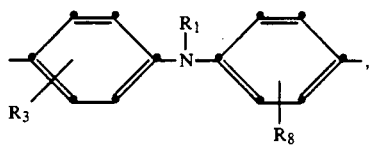
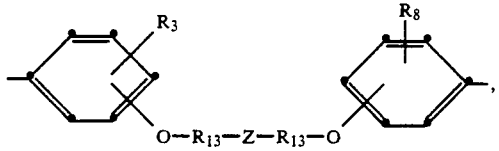
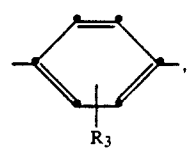
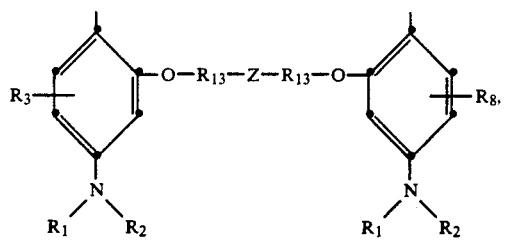
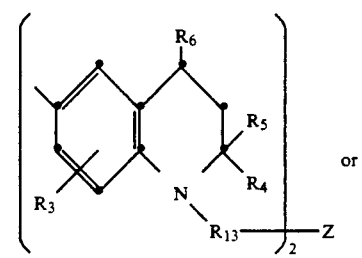

-continued

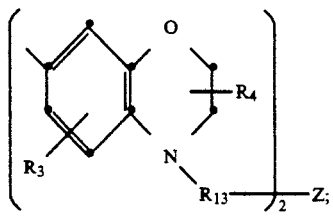

wherein R₁ and R₂ are selected from alkyl, alkenyl, alkynyl, cycloalkyl, phenyl, alkyl substituted with one or more of the following groups:

cycloalkyl; cycloalkyl substituted by a group selected from the group consisting of lower alkyl, lower alkoxy, hydroxy, and alkanoyloxy; phenyl; phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; cyano; halogen; 2-pyrrolidino; phthalimidino; vinylsulfonyl; acrylamido; o-benzoic sulfimido; alkoxy; alkoxyalkoxy; cyanoalkoxy; hydroxy; hydroxyalkoxy; phenoxy; phenoxy substituted with lower alkyl, lower alkoxy or halogen; groups of the formulae:

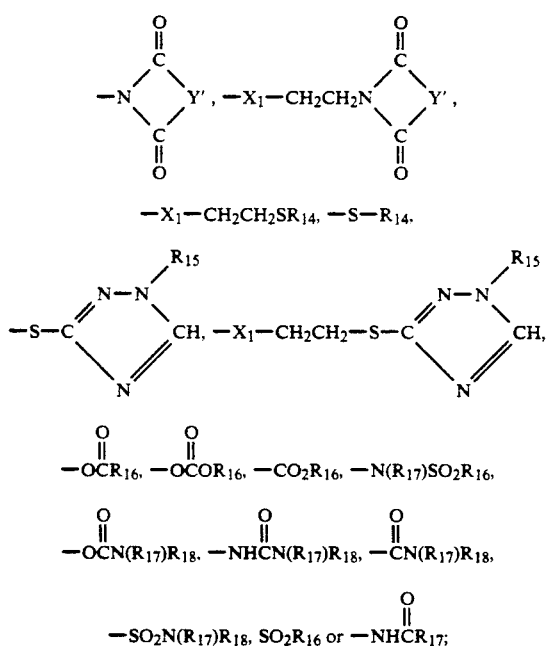

wherein X₁ is selected from —O—, —S— or —SO₂—; Y₁ is selected from C₂-C₃ alkylene, vinylene, o-phenylene and o-phenylene substituted with lower alkyl, lower alkoxy, halogen, carboxy, alkoxycarbonyl or nitro; —OCH₂—; —OCH₂CH₂—; —CH₂OCH₂—; —S—CH₂; —CH₂SCH₂—; —NHCH₂—; —NHCH₂CH₂—; —N(alkyl)CH₂—; —N(alkyl)CH₂CH₂— or NHC(C₆H₅)₂—;

wherein R₁₄ is selected from lower alkyl; cycloalkyl; phenyl; phenyl substituted with one or more groups selected from lower alkyl, lower alkoxy or halogen; a heterocyclic ring selected from pyridyl, pyrimidinyl, benzoxazolyl, benzothiazolyl, benzimidazol, 1,3,4-thiadiazolyl, and 1,3,4-oxadiazolyl, said heterocyclic ring optionally substituted with one or more groups selected from lower alkyl, lower alkoxy or halogen;

R₁₅ is selected from hydrogen, lower alkyl; alkyl substituted with hydroxy, alkanoyloxy, lower alkoxy, halogen, cyano, carbalkoxy or phenyl;

R₁₆ is selected from cycloalkyl; cycloalkyl substituted with lower alkyl; allyl; phenyl; phenyl substituted with one or more groups selected from lower alkyl, lower alkoxy or halogen, lower alkyl; lower alkyl substituted with one or more groups selected from lower alkoxy, halogen, phenyl, cyano, cycloalkyl, phenoxy, lower alkylthio, hydroxy, alkanoyloxy, alkoxycarbonyl or lower alkylsulfonyl;

and R₁₇ and R₁₈ are each independently selected from hydrogen or those groups represented by R₁₆; cycloalkyl substituted with one or more groups selected from the group consisting of lower alkyl, lower alkoxy, hydroxy, and alkanoyloxy; and phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; or R₁ and R₂ are combined with the nitrogen to which they are attached to form an A radical having the formula

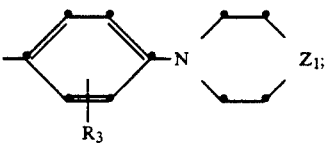

wherein Z₁ is selected from a covalent bond, —CH₂—, —O—, —S—, —SO₂—, —CO—, —CO₂—, —NH—, —N(R₁)—, N(COR₁)— or —N(SO₂R₁)—; R₃ and R₈ are hydrogen or 1-2 substituents selected from lower alkyl, lower alkoxy or halogen; R₄, R₅ and R₆ are hydrogen or lower alkyl; R₇ is hydrogen, lower alkyl, phenyl or phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; R₉ and R₁₀ are selected from hydrogen, lower alkyl, lower alkoxy, hydroxy, halogen or alkanoyloxy; R₁₁ is lower alkyl; phenyl or phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; R₁₂ is hydrogen or 1-2 substituents selected from lower alkyl; lower alkoxy; lower alkylthio; alkenyl; cycloalkyl; lower alkyl substituted with lower alkoxy, hydroxy, alkanoyloxy or phenyl; phenyl; phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; or halogen; R₁₃ is lower alkylene; lower alkylene substituted by one or more lower alkoxy, halogen, phenyl, hydroxy, or alkanoyloxy groups; alkylene oxyalkylene, phenylene; phenylene substituted by a group selected from the group consisting of lower alkoxy, halo, phenyl, hydroxy, and alkanoyloxy; phenylenealkylene; or cycloalkylene; Z is a direct bond, —OCO₂—, —O₂C—, —O—, —SO₂—, —S—, —S—S—, R₁SO₂—N=, —O₂C—lower alkylene —CO₂—, phenylene, —O₂C—phenylene—CO₂—, —O₂C— substituted phenylene—CO₂—, wherein phenylene is substituted by a group selected form the group consisting of lower alkoxy, halo, phenyl, hydroxy, and alkanoyloxy, —O₂CHN—alkylene—NHCO₂—, —O₂CNH—phenylene—NHCO₂— or —O₂CHN—substituted phenylene—NHCO₂—, wherein phenylene is substituted by a group selected from the group consisting of lower alkoxy, halo, phenyl, hydroxy, an alkanoyloxy; L is selected from a direct bond, —O—, —CH₂— or —CH(CH₃)—.

6. The amorphous light absorbing concentrate of claim 5, wherein A is selected from groups of the formula

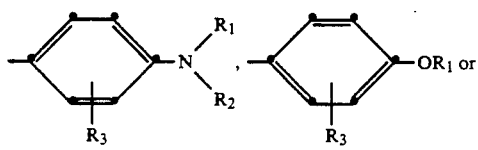

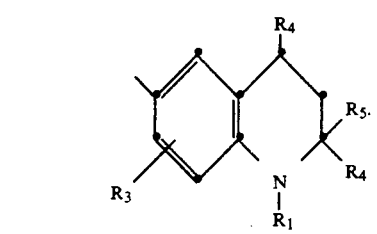

7. The amorphous light absorbing concentrate of claim 5, wherein X is phenyl and Y is a 5-alkoxycarbonylbenzoxazol-2-yl radical.

8. The amorphous light absorbing concentrate of claim 5, wherein X is phenyl and Y is a 5-alkoxycarbonylbenzothiazol-2-yl radical.

9. A light absorbing semicrystalline powder having an average particle diameter of less than about 50 microns comprising a normally-amorphous polyester which has been modified by dissolution-crystallization-precipitation to impart crystallinity thereto, having copolymerized therein at least about 5.0 weight percent of a residue of a light absorbing compound of formulae (II) or (III):

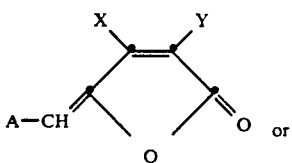

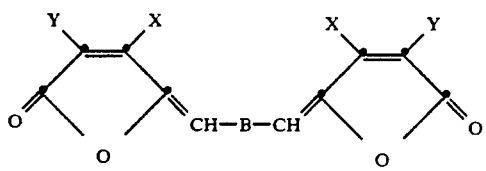

wherein X is phenyl or phenyl substituted by a group selected from the group consisting of lower alkyl; lower alkoxy; halogen; hydroxy; cyano; —NHCOR₁₇; —N(R₁₇)SO₂R₁₆; SO₂R₁₆; —CO₂R₁₆; and lower alkyl substituted with hydroxy, lower alkoxy, halogen or alkanoyloxy, wherein R₁₆ and R₁₇ are as defined below;

wherein Y is benzoxazol-2-yl or benzothiazol-2-yl radical, or a group having the following formula

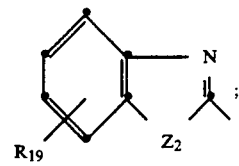

wherein Z₂ is —O— or —S—; R₁₉ is one or more lower alkyl, lower alkoxy, —O—lower alkylene—CO₂R₁₇, lower alkylene—CO₂R₁₇, halo, cyano, —SO₂R₁₆, —NHCOR₁₇, —(R₁₇)SO₂R₁₆, —CO₂R₁₇, —CON(R₁₇)R₁₈, or —SO₂N(R₁₇)R₁₈ groups, wherein R₁₈ is as defined below;

wherein A is selected from groups of the formulae

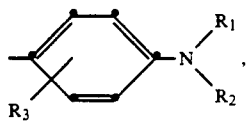

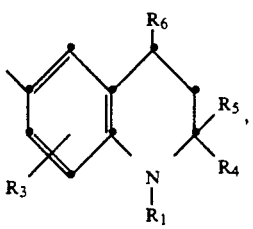

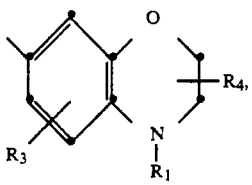

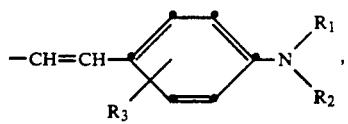

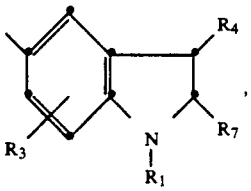

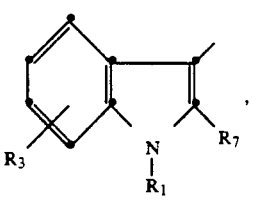

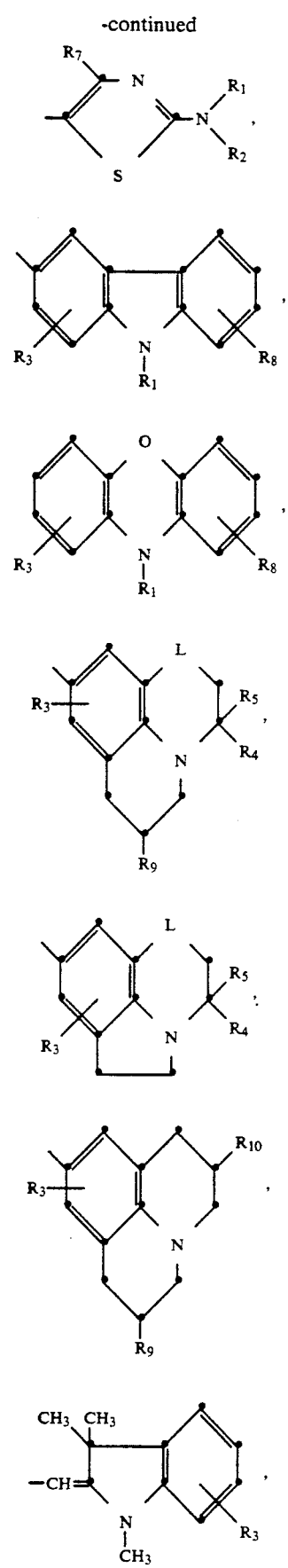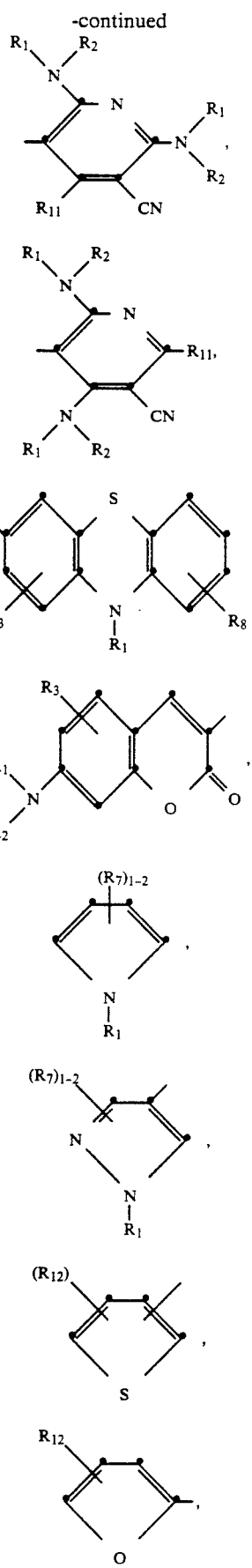

-continued

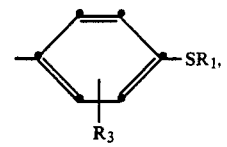

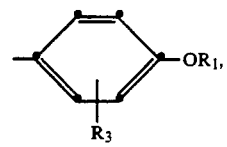

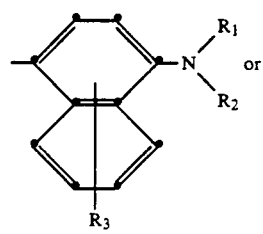

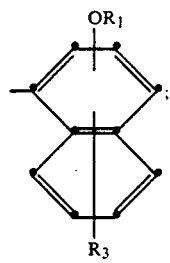

and B is selected from the following formulae:

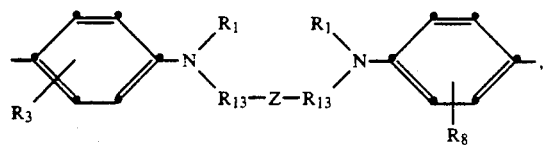

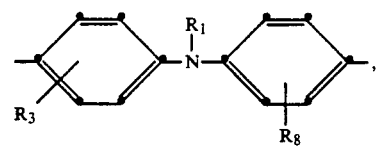

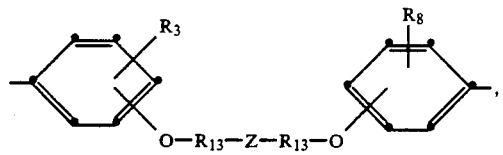

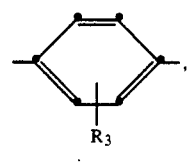

-continued

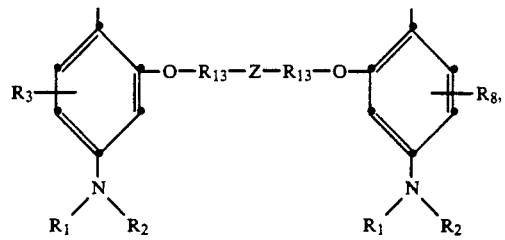

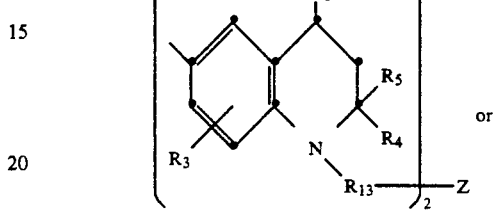

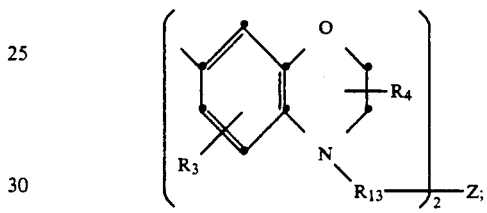

wherein $R_1$ and $R_2$ are selected from alkyl, alkenyl, alkynyl, cycloalkyl, phenyl, alkyl substituted with one or more of the following groups:

cycloalkyl; cycloalkyl substituted by a group selected from the group consisting of lower alkyl, lower alkoxy, hydroxy, and alkanoyloxy; phenyl; phenyl substituted by a group selected from the group consisting of lower alkyl, lower alkoxy, halogen, hydroxy, cyano, —$NHCOR_{17}$, —$N(R_{17})SO_2R_{16}$, —$SO_2R_{16}$, —$CO_2R_{16}$, and lower alkyl substituted with hydroxy, lower alkoxy, halogen or alkanoyloxy; cyano; halogen; 2-pyrrolidino; phthalimidino; vinylsulfonyl; acrylamido; o-benzoic sulfimido; alkoxy; alkoxyalkoxy; cyanoalkoxy; hydroxy; hydroxyalkoxy; phenoxy; phenoxy substituted with lower alkyl, lower alkoxy or halogen; groups of the formulae:

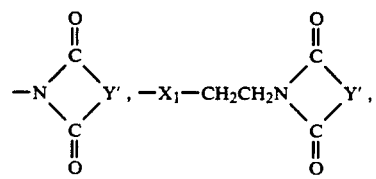

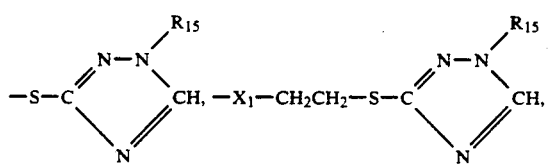

-continued

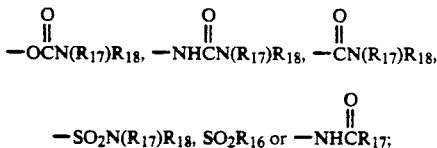

$$-SO_2N(R_{17})R_{18}, SO_2R_{16} \text{ or } -NHCR_{17};$$

wherein $X_1$ is selected from $-O-$, $-S-$ or $-SO_2-$; $Y_1$ is selected from $C_2-C_3$ alkylene, vinylene, o-phenylene and o-phenylene substituted with lower alkyl, lower alkoxy, halogen, carboxy, alkoxycarbonyl or nitro; $-OCH_2-$; $-OCH_2CH_2-$; $-CH_2OCH_2-$; $-S-CH_2-$; $-CH_2SCH_2$; $-NHCH_2$; $-NHCH_2CH_2$; $-N(alkyl)CH_2-$; $-N(alkyl)CH_2CH_2-$ or $NHC(C_6H_5)_2-$;

wherein $R_{14}$ is selected from lower alkyl; cycloalkyl; phenyl; phenyl substituted with one or more groups selected from lower alkyl, lower alkoxy or halogen; a heterocyclic ring selected from pyridyl, pyrimidinyl, benzoxazolyl, benzothiazolyl, benzimidazol, 1,3,4-thiadiazolyl, and 1,3,4-oxadiazolyl, said heterocyclic rings optionally substituted with one or more groups selected from lower alkyl, lower alkoxy or halogen;

$R_{15}$ is selected from hydrogen, lower alkyl; alkyl substituted with hydroxy, alkanoyloxy, lower alkoxy, halogen, cyano, carbalkoxy or phenyl;

$R_{16}$ is selected from cycloalkyl; cycloalkyl substituted with lower alkyl; allyl; phenyl; phenyl substituted with one or more groups selected from lower alkyl, lower alkoxy or halogen; lower alkyl; lower alkyl substituted with one or more groups selected from lower alkoxy, halogen, phenyl, cyano, cycloalkyl, phenoxy, lower alkylthio, hydroxy, alkanoyloxy, alkoxycarbonyl or lower alkylsulfonyl;

and $R_{17}$ and $R_{18}$ are each independently selected from hydrogen or those groups represented by $R_{16}$; cycloalkyl substituted with one or more groups selected from the group consisting of lower alkyl, lower alkoxy, hydroxy, and alkanoyloxy; and phenyl substituted by a group selected from the group consisting of lower alkyl, lower alkoxy, halogen, hydroxy, cyano, $-NHCOR_{17}$, $-N(R_{17})SO_2R_{16}$, $-SO_2R_{16}$, $-CO_2R_{16}$, and lower alkyl substituted with hydroxy, lower alkoxy, halogen or alkanoyloxy; or $R_1$ and $R_2$ are combined with the nitrogen to which they are attached to form an A radical having the formula

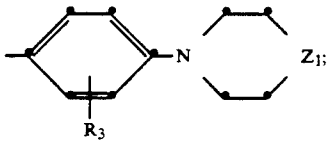

wherein $Z_1$ is selected from a covalent bond, $-CH_2-$, $-O-$, $-S-$, $-SO_2-$, $-CO-$, $-CO_2-$, $-NH-$, $-N(R_1)-$, $N(COR_1)-$ or $-N(SO_2R_1)-$; $R_3$ and $R_8$ are hydrogen or 1-2 substituents selected from lower alkyl, lower alkoxy or halogen; $R_4$, $R_5$ and $R_6$ are hydrogen or lower alkyl; $R_7$ is hydrogen, lower alkyl, phenyl or phenyl substituted by a group selected from the group consisting of lower alkyl, lower alkoxy, halogen, hydroxy, cyano, $-NHCOR_{17}$, $-N(R_{17})SO_2R_{16}$, $-SO_2R_{16}$, $-CO_2R_{16}$, and lower alkyl substituted with hydroxy, lower alkoxy, halogen or alkanoyloxy; $R_9$ and $R_{10}$ are selected from hydrogen, lower alkyl, lower alkoxy, hydroxy, halogen or alkanoyloxy; $R_{11}$ is lower alkyl; phenyl or phenyl substituted by a group selected from the group consisting of lower alkyl, lower alkoxy, halogen, hydroxy, cyano, $-NHCOR_{17}$, $-N(R_{17})SO_2R_{16}$, $-SO_2R_{16}$, $-CO_2R_{16}$, and lower alkyl substituted with hydroxy, lower alkoxy, halogen or alkanoyloxy; $R_{12}$ is hydrogen or 1-2 substituents selected from lower alkyl; lower alkoxy; lower alkylthio; alkenyl; cycloalkyl; lower alkyl substituted with lower alkoxy, hydroxy, alkanoyloxy or phenyl; phenyl; phenyl substituted by a group selected from the group consisting of lower alkyl, lower alkoxy, halogen, hydroxy, cyano, $-NHCOR_{17}$, $-N(R_{17})SO_2R_{16}$, $-SO_2R_{16}$, $-CO_2R_{16}$, and lower alkyl substituted with hydroxy, lower alkoxy, halogen or alkanoyloxy; or halogen; $R_{13}$ is lower alkylene; lower alkylene substituted by one or more lower alkoxy, halogen, phenyl, hydroxy, or alkanoyloxy groups; alkylene oxyalkylene, phenylene; phenylene substituted by a group selected from the group consisting of lower alkoxy, halo, phenyl, hydroxy, and alkanoyloxy; phenylenealkylene; or cycloalkylene; Z is a direct bond, $-OCO_2-$, $-O_2C-$, $-O-$, $-SO_2-$, $-S-$, $-S-S-$, $R_1SO_2-N=$, $-O_2C-$ lower alkylene $-CO_2-$, phenylene, $-O_2C-$phenylene$-CO_2-$, $-O_2C-$ substituted phenylene$-CO_2-$, wherein phenylene is substituted by a group selected form the group consisting of lower alkoxy, halo, phenyl, hydroxy, and alkanoyloxy; $-O_2CNH-$alkylene$-NHCO_2-$, $-O_2CNH-$phenylene-$NHCO_2-$ or $-O_2CNH-$substituted phenylene$-NHCO_2-$, wherein phenylene is substituted by a group selected from the group consisting of lower alkoxy, halo phenyl, hydroxy, and alkanoyloxy; L is selected from a direct bond, $-O-$, $-CH_2-$ or $-CH(CH_3)-$.

10. The light absorbing semicrystalline powder of claim 9, wherein A is a selected from groups of the formulae

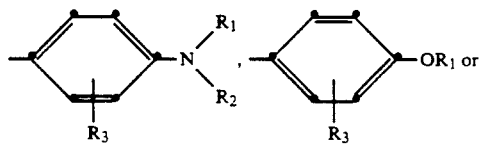

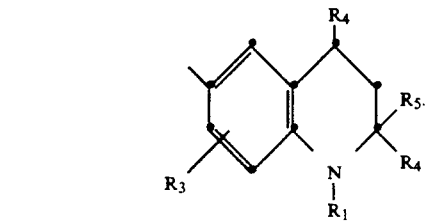

11. The light absorbing semicrystalline powder of claim 9, wherein X is phenyl an Y is a 5-alkoxycarbonylbenzoxazol-2-yl radical.

12. The light absorbing semicrystalline powder of claim 9, wherein X is phenyl and Y is a 5-alkoxycarbonylbenzoxazol-2-yl radical.

13. A shaped or formed article comprised of polyester composition having copolymerization therein at least 0.001 weight percent of a residue of a light absorbing compound of formulae (II) or (III):

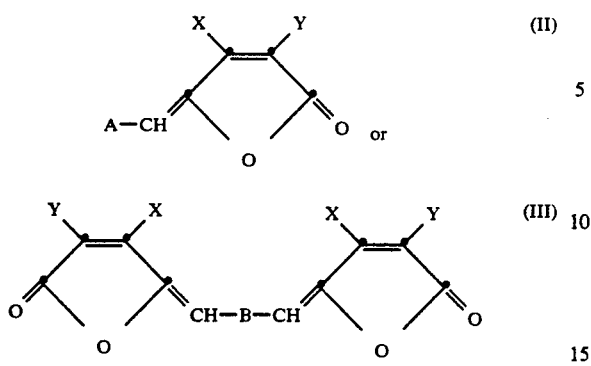

wherein X is phenyl or phenyl substituted by a group selected from the group consisting of lower alkyl; lower alkoxy; halogen; hydroxy; cyano; —NHCOR$_{17}$; —N(R$_{17}$)SO$_2$R$_{16}$; —SO$_2$R$_{16}$; —CO$_2$R$_{16}$; and lower alkyl substituted with hydroxy, lower alkoxy, halogen or alkanoyloxy, wherein R$_{16}$ and R$_{17}$ are as defined below;

wherein Y is a benzoxazol-2-yl or benzothiazol-2-yl radical, or a group having the following formula

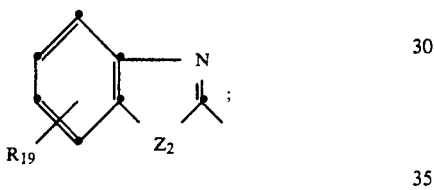

wherein Z$_2$ is —O— or —S—; R$_{19}$ is one or more lower alkyl, lower alkoxy, —O—lower alkylene—CO$_2$R$_{17}$, lower alkylene—CO$_2$R$_{17}$, halo, cyano, —SO$_2$R$_{16}$, —NHCOR$_{17}$, —(R$_{17}$)SO$_2$R$_{16}$, —CO$_2$R$_{17}$, —CON(R$_{17}$)R$_{18}$, or —SO$_2$N(R$_{17}$)R$_{18}$ groups, wherein R$_{18}$ is as defined below;

wherein A is selected from groups of the formulae

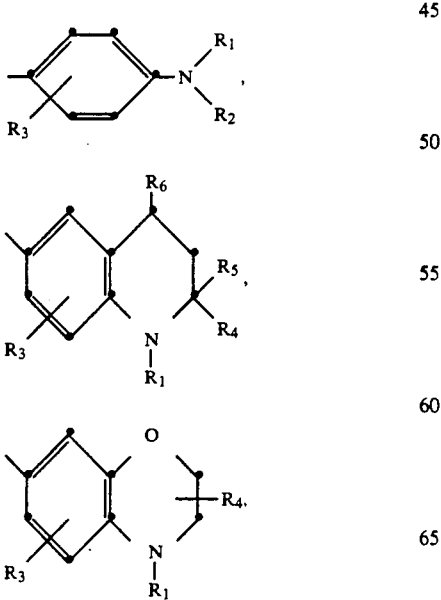

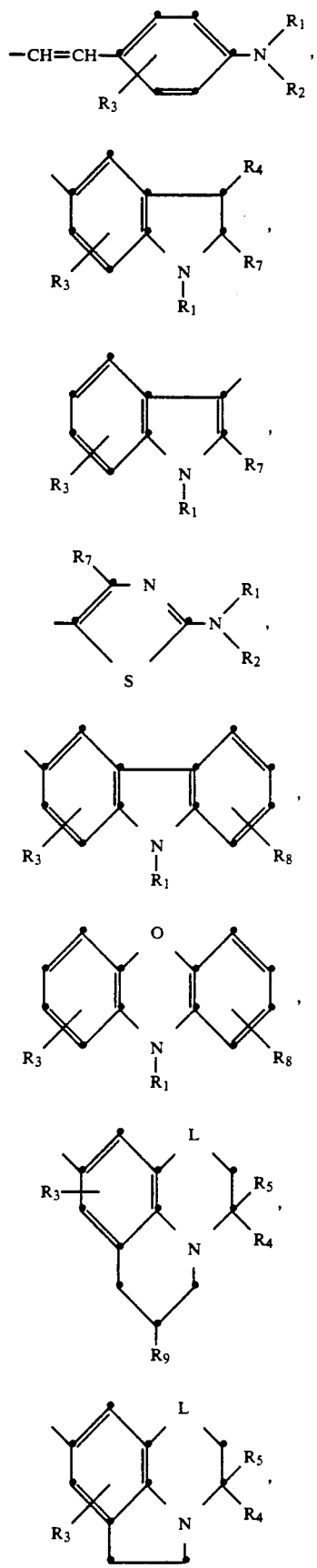

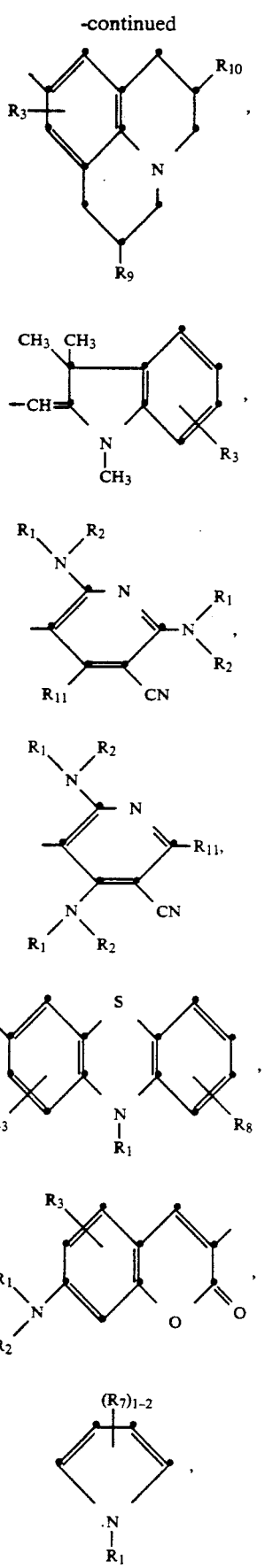
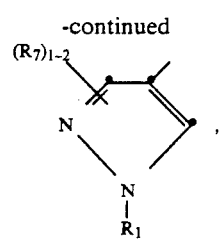
and B is selected from the following formulae:
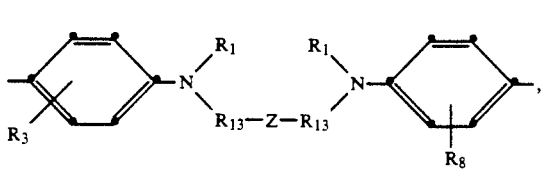
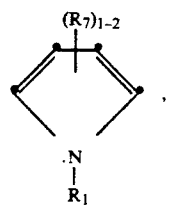

83

-continued

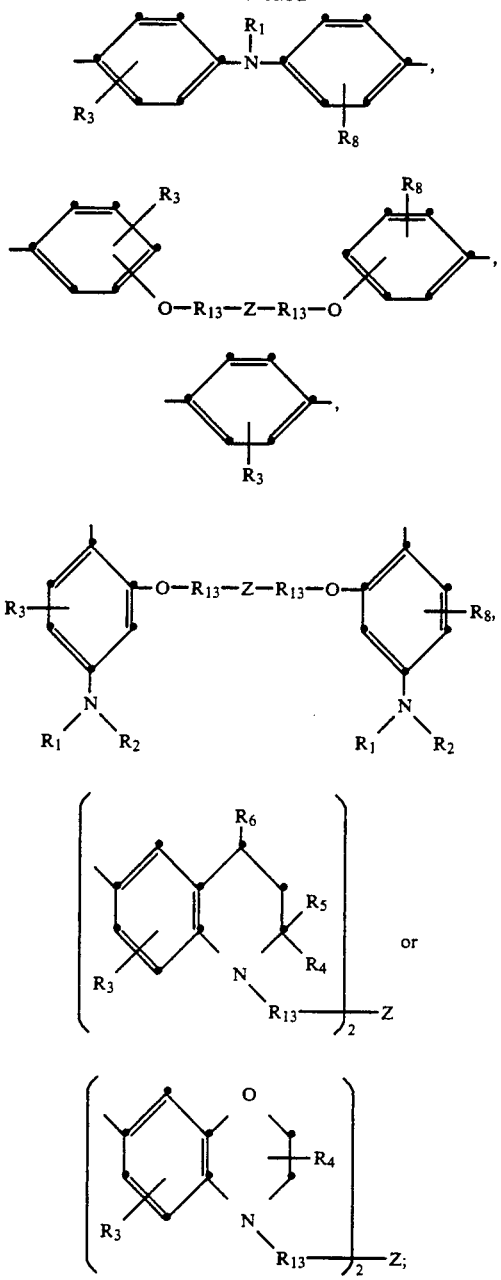

wherein R₁ and R₂ are selected from alkyl, alkenyl, alkynyl, cycloalkyl, phenyl, alkyl substituted with one or more of the following groups:

cycloalkyl; cycloalkyl substituted by a group selected from the group consisting of lower alkyl, lower alkoxy, hydroxy, and alkanoyloxy; phenyl; phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; cyano; halogen; 2-pyrrolidino; phthalimidino; vinylsulfonyl; acrylamido; o-benzoic sulfimido; alkoxy; alkoxyalkoxy; cyanoalkoxy; hydroxy; hydroxyalkoxy; phenoxy; phenoxy substituted with lower alkyl, lower alkoxy or halogen; groups of the formulae:

84

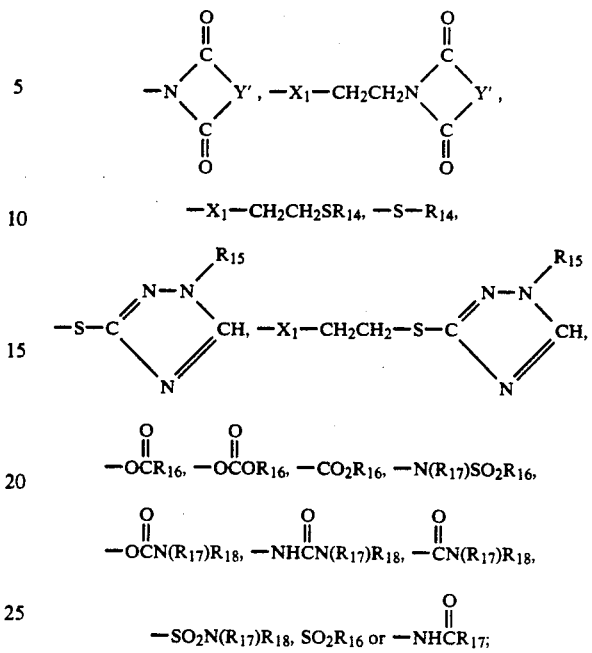

—X₁—CH₂CH₂SR₁₄, —S—R₁₄,

—OCR₁₆, —OCOR₁₆, —CO₂R₁₆, —N(R₁₇)SO₂R₁₆,

—OCN(R₁₇)R₁₈, —NHCN(R₁₇)R₁₈, —CN(R₁₇)R₁₈,

—SO₂N(R₁₇)R₁₈, SO₂R₁₆ or —NHCR₁₇;

wherein X₁ is selected from —O—, —S— or —SO₂—; Y₁ is selected from C₂-C₃ alkylene, vinylene, o-phenylene an o-phenylene substituted with lower alkyl, lower alkoxy, halogen, carboxy, alkoxycarbonyl or nitro; —OCH₂—; —OCH₂CH₂—; —CH₂OCH₂—; —S—CH₂—; —CH₂SCH₂—; —NHCH₂—; —NHCH₂CH₂—; —N(alkyl)CH₂—; —N(alkyl)CH₂CH₂— or NHC(C₆H₅)₂—;

wherein R₁₄ is selected from lower alkyl; cycloalkyl; phenyl; phenyl substituted with one or more groups selected from lower alkyl, lower alkoxy or halogen; a heterocyclic ring selected from pyridyl, pyrimidinyl, benzoxazolyl, benzothiazolyl, benzimidazol, 1,3,4-thiadiazolyl, and 1,3,4-oxadiazolyl, said heterocyclic ring optionally substituted with one or more groups selected from lower alkyl, lower alkoxy or halogen;

R₁₅ is selected from hydrogen, lower alkyl; alkyl substituted with hydroxy, alkanoyloxy, lower alkoxy, halogen, cyano, carbalkoxy or phenyl;

R₁₆ is selected from cycloalkyl; cycloalkyl substituted with lower alkyl; allyl; phenyl; phenyl substituted with one or more groups selected from lower alkyl, lower alkoxy or halogen; lower alkyl; lower alkyl substituted with one or more groups selected from lower alkoxy, halogen, phenyl, cyano, cycloalkyl, phenoxy, lower alkylthio, hydroxy, alkanoyloxy, alkoxycarbonyl or lower alkylsulfonyl;

and R₁₇ and R₁₈ are each independently selected from hydrogen or those groups represented by R₁₆; cycloalkyl substituted with one or more groups selected from the group consisting of lower alkyl, lower alkoxy, hydroxy, and alkanoyloxy; and phenyl substituted by a group selected from the group consisting of lower alkyl, lower alkoxy, halogen, hydroxy, cyano, —NHCOR₁₇, —N(R₁₇)SO₂R₁₆, —SO₂R₁₆, —CO₂R₁₆, and lower alkyl substituted with hydroxy, lower alkoxy, halogen or alkanoyloxy; or R₁ and R₂ are combined with the nitrogen to which they are attached to form an A radical having the formula

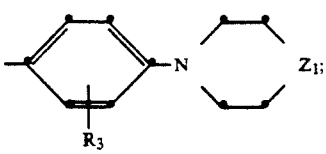

wherein $Z_1$ is selected from a covalent bond, —CH$_2$—, —O—, —S—, —SO$_2$—, —CO—, —CO$_2$—, —NH—, —N(R$_1$)—, N(COR$_1$)— or —N(SO$_2$R$_1$)—; $R_3$ and $R_8$ are hydrogen or 1–2 substituents selected from lower alkyl, lower alkoxy or halogen; $R_4$, $R_5$ and $R_6$ are hydrogen or lower alkyl; $R_7$ is hydrogen, lower alkyl, phenyl or phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; $R_9$ and $R_{10}$ are selected from hydrogen, lower alkyl, lower alkoxy, hydroxy, halogen or alkanoyloxy; $R_{11}$ is lower alkyl; phenyl or phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; $R_{12}$ is hydrogen or 1–2 substituents selected from lower alkyl; lower alkoxy; lower alkylthio; alkenyl; cycloalkyl; lower alkyl substituted with lower alkoxy, hydroxy, alkanoyloxy or phenyl; phenyl; phenyl substituted by a group selected from the group consisting of lower alkyl, lower alkoxy, halogen, hydroxy, cyano, —NHCOR$_{17}$, —N(R$_{17}$)SO$_2$R$_{16}$, —SO$_2$R$_{16}$, —CO$_2$R$_{16}$, and lower alkyl substituted with hydroxy, lower alkoxy, halogen or alkanoyloxy; or halogen; $R_{13}$ is lower alkylene; lower alkylene substituted by one or more lower alkoxy, halogen, phenyl, hydroxy, or alkanoyloxy groups; alkylene oxyalkylene, phenylene; phenylene substituted by a group selected from the group consisting of lower alkoxy, halo, phenyl, hydroxy, and alkanoyloxy; phenylenealkylene; or cycloalkylene; Z is a direct bond, —OCO$_2$—, —O$_2$C—, —O—, —SO$_2$—, —S—, —S—S—, R$_1$SO$_2$—N=, —O$_2$C— lower alkylene —CO$_2$—, phenylene, —O$_2$C—phenylene—CO$_2$—, —O$_2$C—substituted phenylene—CO$_2$—, wherein phenylene is substituted by a group selected form the group consisting of lower alkoxy, halo, phenyl, hydroxy, and alkanoyloxy, —O$_2$CNH—alkylene—NHCO$_2$—, —O$_2$CNH—phenylene—NHCO$_2$— or —O$_2$CNH—substituted phenylene—NHCO$_2$—, wherein phenylene is substituted by a group selected from the group consisting of lower alkoxy, halo, phenyl, hydroxy, and alkanoyloxy, L is selected from a direct bond, —O—, —CH$_2$— or —CH(CH$_3$)—.

14. The article of claim 13, wherein A is selected from groups of the formula

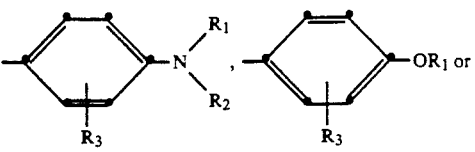

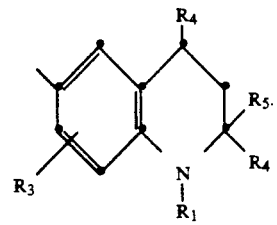

15. The article of claim 14, wherein X is phenyl and Y is a 5-alkoxycarbonylbenzoxazol-2-yl radical.

16. The article of claim 14, wherein X is phenyl and Y is a 5-alkoxycarbonylbenzothiazol-2-yl radical.

17. A light absorbing thermoplastic polymer composition which comprises one or more thermoplastic polymers and one or more colored polyester compositions of claim 1.

18. The light absorbing thermoplastic polymer composition of claim 17 wherein the thermoplastic polymer is selected from a list consisting of polyesters, polyolefins, polyamides, polyimides, polyvinyl chloride, polyvinylidene chloride, polyurethanes, polycarbonates, cellulose esters, polyacrylates, polyvinylesters, polyester-amides, polystyrene, acrylonitrile butadiene-styrene, and styrene acrylonitrile.

19. The light absorbing thermoplastic polymer composition of claim 17, wherein the thermoplastic polymer is a polyolefin.

20. The light absorbing thermoplastic polymer composition of claim 17, wherein the polyolefin is polyethylene, polypropylene, or polybutylene.

21. The polyester of claim 1, wherein the compound of formula (II) is

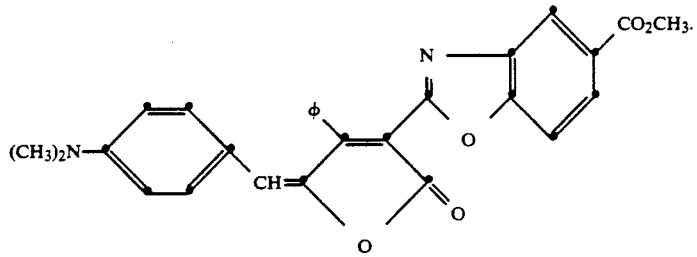

22. The light absorbing thermoplastic polymer composition of claim 17, wherein at least one of the thermoplastic polymers is a polyamide.

23. The light absorbing thermoplastic polymer composition of claim 17, wherein at least one of the thermoplastic polymers is a polyurethane.

24. The light absorbing thermoplastic polymer composition of claim 17, wherein at least one of the thermoplastic polymers is polyvinyl chloride.

25. The light absorbing thermoplastic polymer composition of claim 17, wherein at least one of the thermoplastic polymers is polyvinylidene chloride.

26. The light absorbing thermoplastic polymer composition of claim 17, wherein at least one of the thermoplastic polymers is a polycarbonate.

27. The light absorbing thermoplastic polymer composition of claim 17, wherein at least one of the thermoplastic polymers is a polyester.

28. The light absorbing thermoplastic polymer composition of claim 17, wherein at least one of the thermoplastic polymers is a cellulose ester or mixtures thereof.

29. The light absorbing thermoplastic polymer composition of claim 17, wherein at least one of the thermoplastic polymers is selected from a list consisting of cellulose acetate, cellulose propionate, cellulose butyrate, cellulose acetate, propionate, and cellulose acetate, butyrate.

30. The light absorbing thermoplastic polymer composition of claim 17, wherein at least one of the thermoplastic polymers is a polyacrylate.

31. The light absorbing thermoplastic polymer composition of claim 17, wherein at least one of the thermoplastic polymers is a polyester amide.

32. The light absorbing thermoplastic polymer composition of claim 17, wherein at least one of the thermoplastic polymers is polystyrene.

33. The light absorbing thermoplastic polymer composition of claim 17, wherein the thermoplastic polymer is a blend of a polyester and a polycarbonate.

* * * * *